(12) United States Patent
Uchiyama

(10) Patent No.: US 10,183,125 B2
(45) Date of Patent: Jan. 22, 2019

(54) PUNCTURE DEVICE AND MEDICAL FLUID ADMINISTRATION DEVICE

(71) Applicant: Terumo Kabushiki Kaisha, Tokyo (JP)

(72) Inventor: Joji Uchiyama, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 644 days.

(21) Appl. No.: 14/671,339

(22) Filed: Mar. 27, 2015

(65) Prior Publication Data
US 2015/0196719 A1 Jul. 16, 2015

Related U.S. Application Data

(63) Continuation of application No. PCT/JP2012/075871, filed on Sep. 28, 2012.

(51) Int. Cl.
*A61M 5/32* (2006.01)
*A61M 5/142* (2006.01)
(Continued)

(52) U.S. Cl.
CPC ............ *A61M 5/3287* (2013.01); *A61B 5/07* (2013.01); *A61M 5/14248* (2013.01);
(Continued)

(58) Field of Classification Search
CPC ............... A61M 5/158; A61M 5/1582; A61M 5/14248; A61M 5/1452;
(Continued)

(56) References Cited

U.S. PATENT DOCUMENTS

2008/0319414 A1 12/2008 Yodfat et al.
2010/0137695 A1* 6/2010 Yodfat ................. A61B 5/6849
600/345
(Continued)

FOREIGN PATENT DOCUMENTS

JP 2002-058747 A 2/2002
JP 2009-201539 A 9/2009
(Continued)

OTHER PUBLICATIONS

Office Communication dated Mar. 5, 2016 in corresponding European Patent Application No. 12 885 681.2.
Notification of Reasons for Refusal dated Jun. 28, 2016 in corresponding Japanese Patent Application No. 2014-538077.
International Search Report dated Nov. 6, 2012 issued in Application No. PCT/JP2012/075871.

*Primary Examiner* — Kevin C Sirmons
*Assistant Examiner* — Leah Swanson
(74) *Attorney, Agent, or Firm* — Foley & Lardner LLP

(57) ABSTRACT

A puncture device includes a housing unit including an attachment surface configured to be attached to a body surface of a user; a puncture needle including an outer needle and an inner catheter located in the outer needle, the puncture needle being configured to be projected from the attachment surface to be punctured into a body of the user; a puncture mechanism configured to project the puncture needle from the attachment surface to be punctured into the body of the user, and pull back only the outer needle of the puncture needle into the housing unit with the inner catheter of the puncture needle indwelled in the body; and a puncture angle adjustment mechanism configured to adjust a puncture angle of the puncture needle, which is an angle of the puncture needle with respect to the attachment surface.

10 Claims, 24 Drawing Sheets

(51) Int. Cl.
*A61M 25/06* (2006.01)
*A61B 5/07* (2006.01)
*A61M 5/158* (2006.01)
*A61M 5/145* (2006.01)

(52) U.S. Cl.
CPC ........ *A61M 5/158* (2013.01); *A61M 25/0662* (2013.01); *A61M 5/1452* (2013.01); *A61M 2005/14252* (2013.01); *A61M 2005/1583* (2013.01); *A61M 2005/1585* (2013.01); *A61M 2005/3289* (2013.01); *A61M 2025/0681* (2013.01)

(58) Field of Classification Search
CPC .. A61M 2005/1583; A61M 2005/1585; A61M 5/3287; A61M 2005/14252
USPC .......................................................... 604/151
See application file for complete search history.

(56) References Cited

U.S. PATENT DOCUMENTS

| | | | |
|---|---|---|---|
| 2010/0324392 A1* | 12/2010 | Yee | A61B 5/14532 600/345 |
| 2010/0331824 A1 | 12/2010 | Moberg et al. | |
| 2011/0288574 A1* | 11/2011 | Curry | A61B 5/15194 606/185 |

FOREIGN PATENT DOCUMENTS

| JP | 2009-545341 A | 12/2009 |
|---|---|---|
| JP | 2010-501283 A | 1/2010 |
| WO | WO-2008/014791 A1 | 2/2008 |
| WO | WO-2008/024814 A2 | 2/2008 |
| WO | WO-2010/019795 A2 | 2/2010 |

* cited by examiner

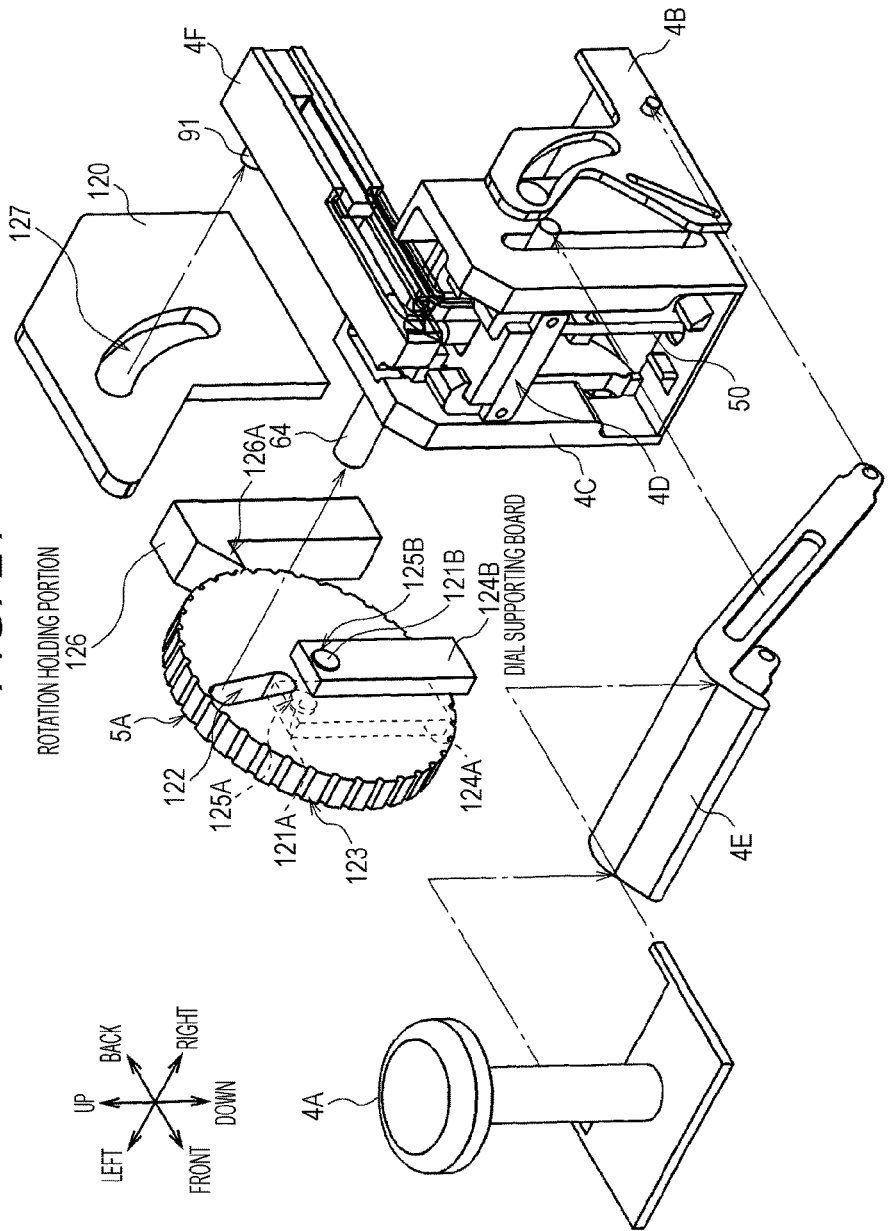

PUNCTURE DEVICE AND MEDICAL FLUID ADMINISTRATION DEVICE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/075871 filed on Sep. 28, 2012, the entire contents of which are hereby incorporated by reference in its entirety.

BACKGROUND

Technical Field

The present disclosure relates to a puncture device and a medical fluid administration device. For example, the embodiments of the present invention are suitable for administering insulin into the body.

Background Art

A portable device used by being attached to a body surface of a user has been conventionally proposed as a device for administering medical fluid (insulin), the device being a so-called syringe pump type medical fluid administration device that administers the medical fluid filled in an outer tube into the body by pushing out the medical fluid through a plunger (see e.g., JP 2010-501283).

In the medical fluid administration device, the medical fluid is administered through a puncture needle punctured into the body of the user. A puncture needle having a double structure including an inner needle made of metal and an outer catheter made of plastic has been conventionally proposed for the structure of the puncture needle (see e.g., JP 2002-58747).

The puncture needle having the double structure is punctured into the body of the user with the metal inner needle projected out from a distal end of the plastic outer catheter, and thereafter, the metal inner needle is extracted from the plastic outer catheter, and the medical fluid is administered through the outer catheter with only the outer catheter indwelled in the body of the user.

In the case of the medical fluid administration device used by being attached to the body surface of the user, an angle of a puncture needle, that is, a puncture angle with respect to the attachment surface is desirably adjustable according to the physique, the subcutaneous thickness, and the like of the user in order to fully exert the effect of the medical fluid, because a body shape of the user differs among individuals.

However, in the conventional medical fluid administration device including the puncture needle of a double structure, as described above, the puncture angle is fixed at 30 degrees, for example, and the puncture angle cannot be adjusted. Thus, the effect of the medical fluid may not be fully exerted and the usability is not always satisfactory depending on the body shape of the user, for example.

SUMMARY OF INVENTION

In light of the foregoing, certain embodiments of the present invention provide a puncture device and a medical fluid administration device that can enhance usability.

In one embodiment, a puncture device includes a housing unit including an attachment surface configured to be attached to a body surface of a user; a puncture needle including an outer needle and an inner catheter located in the outer needle, the puncture needle being configured to be projected from the attachment surface to be punctured into a body of the user; a puncture mechanism configured to project the puncture needle, in which a distal end portion of the inner catheter is located in the outer needle, from the attachment surface to be punctured into the body of the user, and pull back only the outer needle of the puncture needle into the housing unit with the inner catheter of the puncture needle indwelled in the body; and a puncture angle adjustment mechanism configured to adjust a puncture angle of the puncture needle, which is an angle of the puncture needle with respect to the attachment surface.

In another embodiment, a medical fluid administration device includes a housing unit including an attachment surface configured to be attached to a body surface of a user; a puncture needle including an outer needle and an inner catheter located in the outer needle, the puncture needle being configured to be projected from the attachment surface to be punctured into a body of the user; a puncture mechanism configured to project the puncture needle, in which a distal end portion of the inner catheter is located in the outer needle, from the attachment surface to be punctured into the body of the user, and pull back only the outer needle of the puncture needle into the housing unit with the inner catheter of the puncture needle indwelled in the body; a medical fluid storage unit configured to store a medical fluid; a feeding unit configured to feed the medical fluid stored in the medical fluid storage unit into the body through the puncture needle; and a puncture angle adjustment mechanism configured to adjust a puncture angle of the puncture needle, which is an angle of the puncture needle with respect to the attachment surface.

In one aspect, the puncture mechanism includes a base configured to act as a guide when sliding the outer needle, the puncture mechanism being configured to cause the puncture needle, in which the distal end portion of the inner catheter is inserted in the outer needle, to project out from the attachment surface by sliding the outer needle along the base.

In one aspect, the puncture angle adjustment mechanism includes a fixed part that is fixed to the housing unit and that supports the base in a freely tillable manner, and the puncture angle adjustment mechanism is configured to adjust the puncture angle by changing a tilt of the base with respect to the fixed part.

In one aspect, the puncture angle adjustment mechanism includes an operation unit that is rotatably operable with respect to the fixed part, and the puncture angle adjustment mechanism is configured to adjust the puncture angle by changing the tilt of the base according to a rotation operation of the operation unit.

In one aspect, the puncture mechanism includes a push-in part configured to be pushed with respect to the housing unit; a center part that is arranged with the outer needle and that slides along the base; and a coupling part that couples the center part and the push-in part. When the push-in part is pushed in with respect to the housing unit, a force with which the push-in part is pushed in is transmitted to the center part and slides the center part via the coupling part to project the puncture needle from the attachment surface.

In one aspect, the center part is held on one end side of the base as an initial position before sliding, the initial position being moved as the base is tilted when changing the puncture angle. The coupling part includes a hole in which a part of the center part is fitted, the coupling part being coupled with the center part by said part of the center part being fitted in the hole. The hole of the coupling part is formed along a movement path of the initial position of the center part, and the puncture mechanism is configured such that the coupling of the push-in part and the center part by the coupling part being maintained constantly as the initial position of the center part is moved and a part of the center part is moved along the hole.

In one aspect, the coupling part is attached in a freely rotating manner with respect to the fixed part, and the coupling part is configured to slide the center part along the base while a part of the center part moves along the hole by rotating with the pushing in of the push-in part.

Thus, the angle of the puncture needle with respect to the attachment surface, that is, the puncture angle can be freely adjusted according to the physique, the subcutaneous thickness, and the like of the user.

According to certain embodiments of the present invention, the angle of the puncture needle with respect to the attachment surface, that is, the puncture angle can be freely adjusted according to the physique, the subcutaneous thickness, and the like of the user, and hence the puncture device and the medical fluid administration device that can enhance the usability can be realized.

BRIEF DESCRIPTION OF DRAWINGS

FIG. 21 is a schematic diagram showing an exploded perspective view of the puncture angle adjustment mechanism.

DETAILED DESCRIPTION

Embodiments of the present invention will be described in detail based on the drawings.

1. Overall Configuration of Medical Fluid Administration Device

Figure 1A:
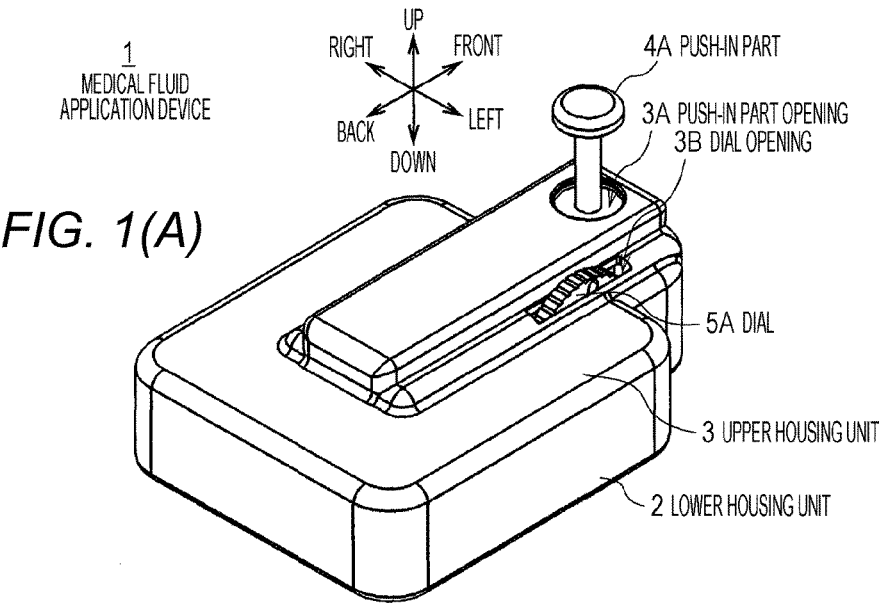
FIGS. 1(A) and 1(B) are schematic diagrams showing a configuration of a medical fluid administration device.
Figure 1B:
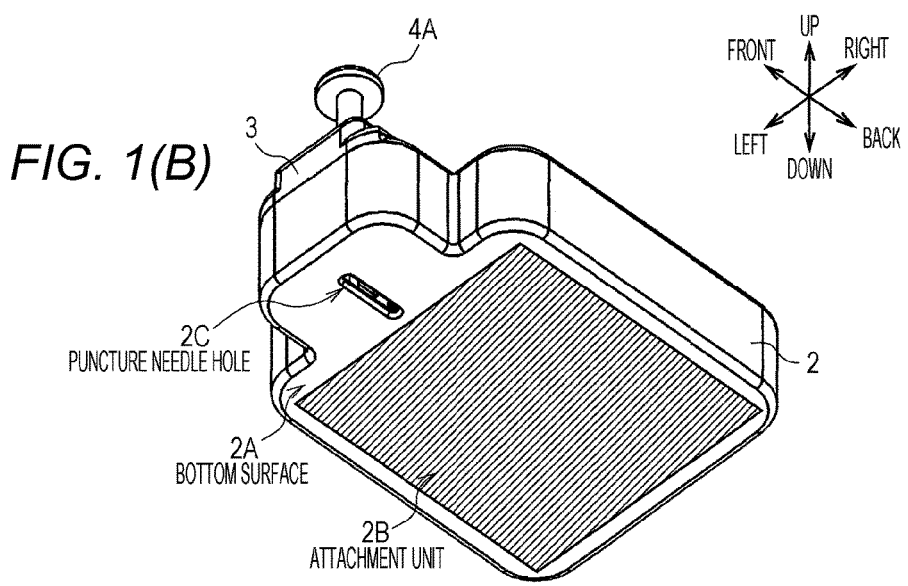
Figure 2:
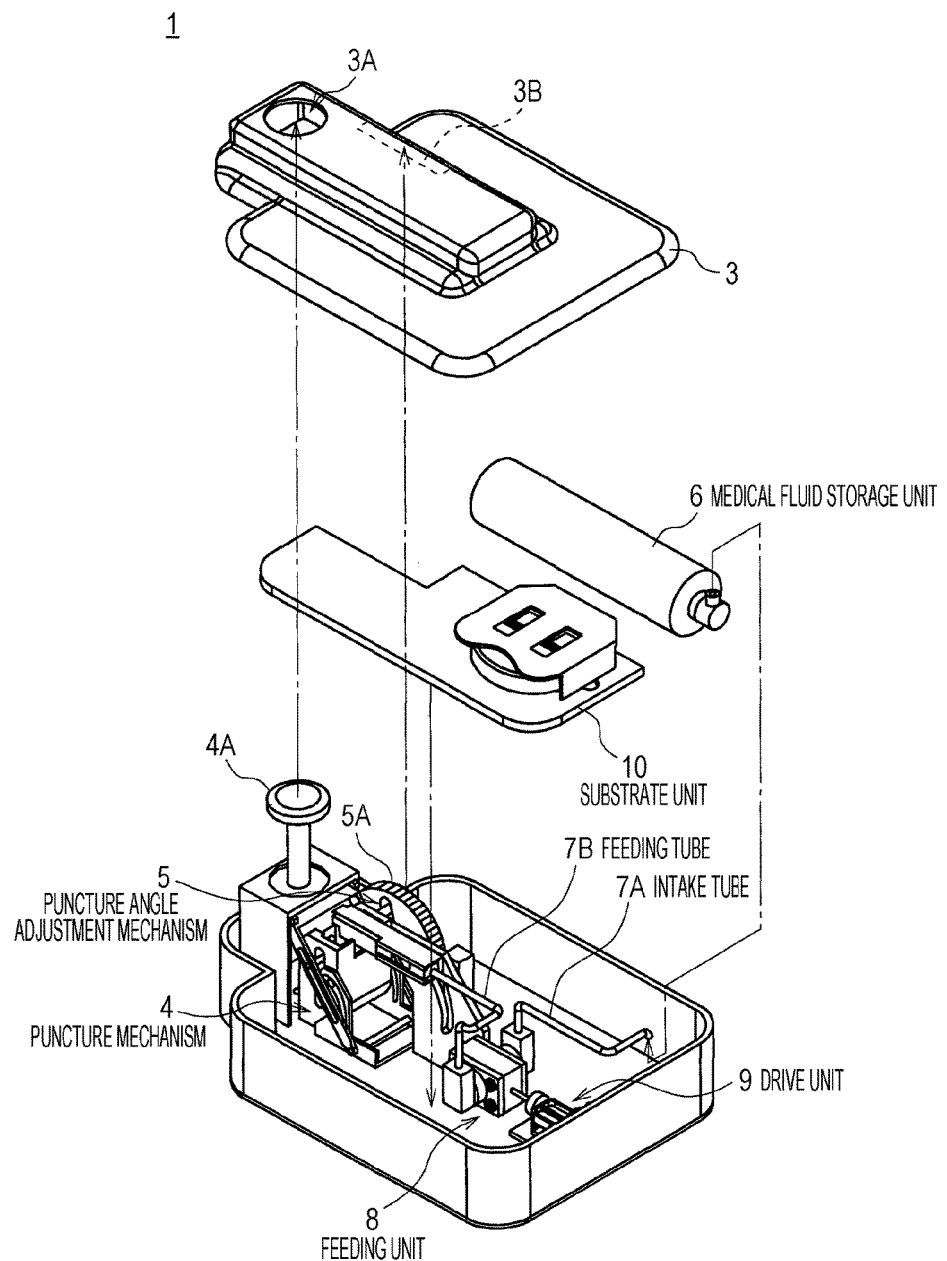
FIG. 2 is an exploded perspective view of the medical fluid administration device.

As shown in FIGS. 1(A) and 1(B) and FIG. 2, a medical fluid administration device 1 is a portable device held and used by being attached to the skin of a user, and is formed in a flat substantially cuboid shape by a lower housing unit 2, in which an upper side is open and a space is interiorly provided, and an upper housing unit 3, which fits into the opening of the lower housing unit 2.

The size of the medical fluid administration device 1 is desirably miniaturized to an extent of being attachable to the skin of the user, and may be a substantially cuboid shape having 32 mm in width, 44 mm in length, and 11 mm in height.

An attachment unit 2B including, for example, double-sided tape, is arranged on a bottom surface 2A of the lower housing unit 2. In the medical fluid administration device 1, the user may hold medical fluid administration device 1 such that the attachment unit 2B is attached to the skin of the user. That is, the attachment unit 2B serves as an attachment surface when attaching the medical fluid administration device 1 to the skin of the user.

The medical fluid administration device 1 includes a puncture needle hole 2C at a front end of the bottom surface 2A of the lower housing unit 2 to enable a puncture needle (not shown), which is to be punctured into the body of the user to administer the interiorly filled insulin into the body of the user, to project out from the interior of the medical fluid administration device 1.

The puncture needle will be described in detail below, but, for example, has a double structure including an outer needle made of metal and an inner catheter made of resin. The puncture needle is projected out from the puncture needle hole 2C and punctured into the body of the user by a puncture mechanism 4 arranged inside the medical fluid administration device 1 shown in FIG. 2, and thereafter, only the outer needle is pulled back into the medical fluid administration device 1 while the inner catheter is indwelled in the body.

The puncture mechanism 4 includes a push-in part 4A that can be push operated, which push-in part 4A projects out to the exterior of the medical fluid administration device 1 from a circular push-in part opening 3A arranged at a front end of the upper housing unit 3.

In the medical fluid administration device 1, the puncture mechanism 4 is operated when the push-in part 4A is pushed in by the user, thus causing the puncture needle to project out from the puncture needle hole 2C.

Furthermore, a puncture angle adjustment mechanism 5 capable of adjusting an angle of the attachment surface and the puncture needle, that is, the puncture angle within a predetermined range (e.g., 90 degrees to 30 degrees) is arranged inside the medical fluid administration device 1.

The puncture angle adjustment mechanism 5 includes a rotatably operable dial 5A. An upper part of the dial 5A is projected out to the exterior of the medical fluid administration device 1 from a rectangular dial opening 3B arranged at a position closer to the right on the back side of the push-in part opening 3A.

In the medical fluid administration device 1, when the dial 5A is rotated by the user, the puncture angle adjustment mechanism 5 is operated thus enabling the puncture angle to be adjusted.

Furthermore, as shown in FIG. 2, a medical fluid storage unit 6, a flow path unit 7, a feeding unit 8, a drive unit 9, a substrate unit 10, and the like are arranged inside the medical fluid administration device 1.

As will be described in detail below, the medical fluid storage unit 6 has the medical fluid externally filled into an outer tube 11 having a cylindrical shape.

The flow path unit 7 includes an intake tube 7A, a feeding tube 7B, flow paths 22B, 23A, 24A formed in the feeding unit 8, and an inner catheter of a puncture needle of the puncture mechanism 4, and forms a flow path through which the medical fluid flows from the medical fluid storage unit 6 into the body. The intake tube 7A communicates the medical fluid storage unit 6 and the flow path 23A formed in the feeding unit 8. The feeding tube 7B communicates the flow path 24A formed in the feeding unit 8 and the inner catheter of the puncture needle of the puncture mechanism 4.

As will be described in detail below, the feeding unit 8 feeds the medical fluid stored in the medical fluid storage unit 6 into the body through the flow path unit 7 when a piston 21 is slidably moved in an internal space 22A of a cylinder part 22 (FIGS. 4(A) and 4(B)).

The drive unit 9 drives the piston 21 based on a control of a CPU 131 (FIG. 24), and slidably moves the piston 21 in the internal space 22A of the cylinder part 22.

The substrate unit 10 is arranged with circuits such as a power supply unit 134 (FIG. 24) for supplying power from a power supply, the CPU 131, and the like.

2. Configuration of Medical Fluid Storage Unit

Figure 3A:
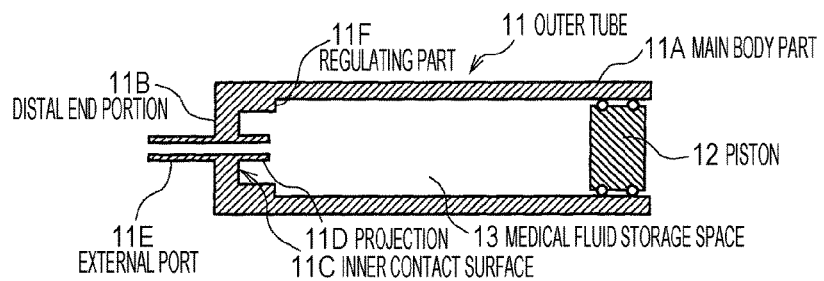
FIGS. 3(A) and 3(B) are schematic diagrams showing a configuration of a medical fluid storage unit.
Figure 3B:
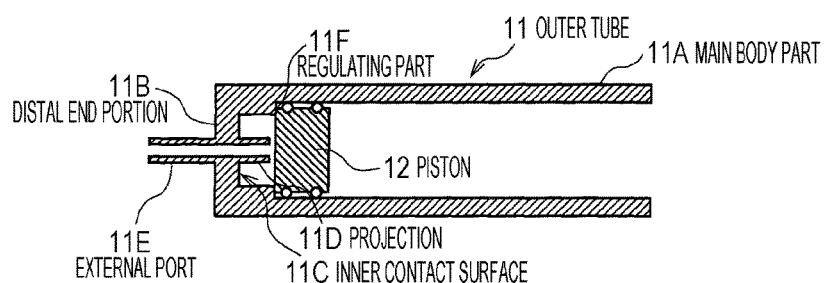

As shown in FIGS. 3(A) and 3(B), the medical fluid storage unit 6 has the piston 12 inserted from an opened end side to the outer tube 11 formed to a cylindrical shape. The medical fluid storage unit 6 stores the medical fluid in a medical fluid storage space 13 formed by the outer tube 11 and the piston 12.

The outer tube 11 has a distal end portion 11B arranged at a distal end of a cylindrical main body part 11A to close the distal end, where the main body part 11A and the distal end portion 11B are integrally formed.

The distal end portion 11B has a hollow projection 11D, with an opening passed to the outside, arranged in a projecting manner at a middle of a surface (hereinafter also referred to as internal contact surface) 11C that makes contact with the medical fluid storage space 13 side along a direction orthogonal to a direction (hereinafter also referred to as tubular axis direction) along the axis of the main body part 11A.

The distal end portion 11B also has a connection port 11E arranged in a projecting manner in a direction opposite to the projection 11D in a manner communicating with the projection 11D, where the intake tube 7A is connected to the connection port 11E.

The main body part 11A includes a regulating part 11F in which a portion longer than a length of the projection 11D is projected out toward the inner side from the inner contact surface 11C in the inner peripheral surface that makes contact with the medical fluid storage space 13. In other words, the main body part 11A is formed such that the inner diameter of the regulating part 11F is smaller than an inner diameter of the portion other than the regulating part 11F in the main body part 11A.

The piston 12 is inserted to the outer tube 11 from a terminal end on the side opposite to the distal end portion 11B, brought into contact along a peripheral direction with an inner side surface of the main body part 11A, and arranged to be liquid tightly and slidably movable along the tube axis direction of the main body part 11A. The piston 12 is formed such that the diameter is greater than the inner diameter of the regulating part 11F.

The medical fluid stored in a vial is injected from a predetermined injection port (not shown) into the medical fluid storage space 13 of the medical fluid storage unit 6 while the piston 12 is positioned on the most distal end portion 11B side and brought into contact with the regulating part 11F. In this case, a slight space is formed by the regulating part 11F between the inner contact surface 11C of the outer tube 11 and the piston 12 in the medical fluid storage unit 6.

In the medical fluid storage unit 6, the piston 12 is moved toward the terminal end side as the medical fluid is injected, and the medical fluid is injected by a predetermined amount (e.g., 2 ml). In this case, the air bubbles that existed in advance remain as is in the medical fluid storage space 13.

When the medical fluid is fed into the body by the feeding unit 8, the medical fluid storage unit 6 feeds the medical fluid to the intake tube 7A through the projection 11D and the connection port 11E while the piston 12 is moved toward the distal end portion 11B side by a medical fluid intake pressure of the feeding unit 8. The medical fluid storage unit 6 feeds the medical fluid until the piston 12 makes contact with the projection 11D.

In the medical fluid storage unit 6, if the air bubbles exist in the medical fluid storage space 13, most of the air bubbles attach to the wall surface. Therefore, in the medical fluid storage unit 6, when the medical fluid is fed by moving the piston 12, the air bubbles attached to the side surface of the main body part 11A move while being pushed by the piston 12, whereby the air bubbles are retained in the space formed between the piston 12 and the inner contact surface 11C when the piston 12 makes contact with the regulating part 11F, thus preventing the air bubbles from being fed to the outside.

Furthermore, the medical fluid storage unit 6 has the projection 11D arranged in a manner projecting to the medical fluid storage space 13 side with respect to the inner contact surface 11C, so that the air bubbles that attached to the side surface of the main body part 11A when feeding the medical fluid can be prevented from being fed to the outside through the opening of the projection 11D.

3. Configuration of Feeding Unit

Figure 4A:
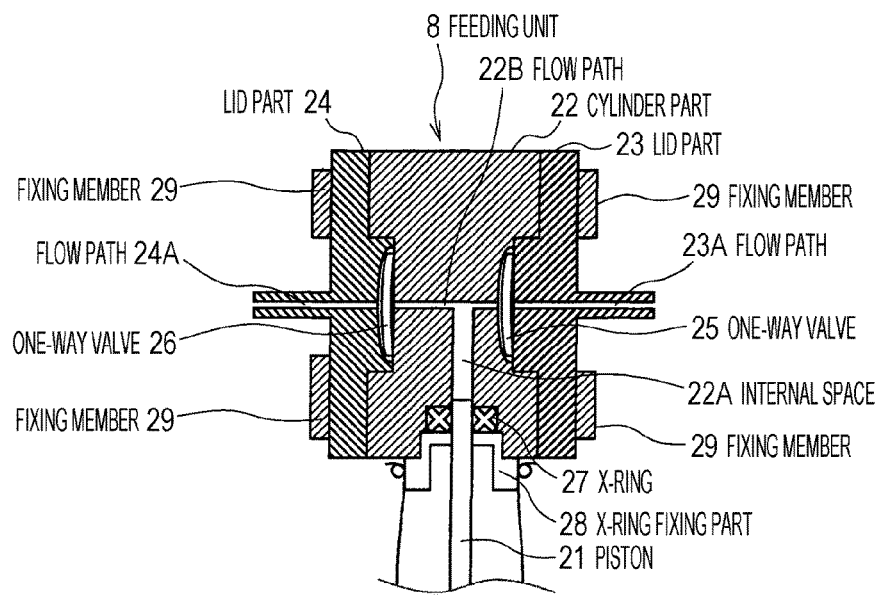
FIGS. 4(A) and 4(B) are schematic diagrams showing a configuration of a feeding unit.

As shown in FIG. 4(A), the feeding unit 8 is configured to include the piston 21, the cylinder part 22, lid parts 23, 24, one-way valves 25, 26, an X-ring 27, an X-ring fixing part 28, and a fixing member 29.

The piston 21 has a diameter of 1.03 mm, for example, and is driven by the drive unit 9 to slidably move at a predetermined stroke in the internal space 22A, which is formed to a hollow circular column shape, formed in the cylinder part 22. The material of the piston 21 may be, for example, stainless steel, copper alloy, aluminum alloy, titanium material, and a thermoplastic elastomer such as polypropylene and polycarbonate, and the like.

The cylinder part 22 includes the internal space 22A in which the piston 21 is inserted from one end and slidably moved. The cylinder part 22 is arranged such that the flow path 22B brought into contact with the other end of the internal space 22A and arranged orthogonal to the internal space 22A passes through the opposing side surfaces of the cylinder part 22.

The cylinder part 22 includes, at one end of the internal space 22A to which the piston 21 is inserted, the X-ring 27 for preventing leakage of the medical fluid between the cylinder part 22 and the piston 21, and the X-ring fixing part 28 for fixing the X-ring 27.

The X-ring 27 is inserted into the cylinder part 22 from a surface side on which the internal space 22A is arranged in the cylinder part 22, and is held down and fixed by the X-ring fixing part 28. The X-ring fixing part 28 fixes the X-ring 27 so that one portion is fitted into the cylinder part 22, and the remaining portion is exposed to the outside.

Figure 4B:
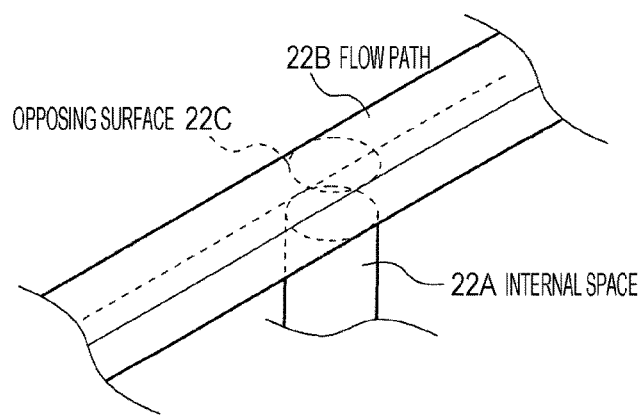

As shown in FIG. 4(B), the flow path 22B is formed to have a rectangular cross-section in which the horizontal width is the same length as the diameter of the internal space 22A, and the height is shorter than a horizontal width. Hydrophilic processing is performed on the surfaces of the internal space 22A and the flow path 22B. For the hydrophilic processing, for example, plasma processing, application of surface acting agent (sodium stearate), and the like are adapted. The hydrophilic processing may also be performed on the distal end face (upper surface) of the piston 21.

In the cylinder part 22, the diameter of the internal space 22A and the horizontal width of the flow path 22B are formed to the same length, and the center position of the axis of the internal space 22A and the center position of the horizontal width of the flow path 22B are coincided.

The cylinder part 22 has the lid parts 23 and 24 connected to the side surface on which the flow path 22B is formed by way of the fixing member 29. The lid parts 23 and 24 include flow paths 23A and 24A passing along the flow path 22B at positions facing the flow path 22B of the cylinder part 22.

The lid part 23 has one end of the flow path 23A connected to the flow path 22B of the cylinder part 22 and the other end of the flow path 23A connected to the intake tube 7A, thus communicating the intake tube 7A and the flow path 22B.

The lid part 24 has one end of the flow path 24A connected to the flow path 22B of the cylinder part 22 and the other end of the flow path 24A connected to the feeding tube 7B, thus communicating the flow path 22B and the feeding tube 7B.

The feeding unit 8 has the one-way valve 25 arranged between the flow path 23A of the lid part 23 and the flow path 22B of the cylinder part 22, and the one-way valve 26 arranged between the flow path 22B of the cylinder part 22 and the flow path 24A of the lid part 24.

The one-way valve 25 passes the medical fluid flowing from the flow path 23A of the lid part 23 to the flow path 22B of the cylinder part 22, but does not pass the medical fluid from the flow path 22B of the cylinder part 22 to the flow path 23A of the lid part 23, and for example, may be an umbrella valve.

The one-way valve 26 passes the medical fluid flowing from the flow path 22B of the cylinder part 22 to the flow path 24A of the lid part 24, but does not pass the medical fluid from the flow path 24A of the lid part 24 to the flow path 22B of the cylinder part 22, and for example, may be an umbrella valve.

When the feeding unit 8 feeds the medical fluid from the medical fluid storage unit 6 into the living body, the piston 21 is moved by the drive unit 9 in the internal space 22A from a position (hereinafter also referred to as push-in position) where the piston 21 is pushed in the most to a position (hereinafter also referred to as pull-back position) where the piston 21 is pulled back the most, thus taking the medical fluid stored in the medical fluid storage unit 6 into the internal space 22A.

The feeding unit 8 feeds the medical fluid taken into the internal space 22A into the living body as the piston 21 is moved by the drive unit 9 from the pull-back position to the push-in position.

The feeding unit 8 can administer the medical fluid of about 1 to 2 µL into the body of the user with the operation of reciprocating the piston 21 once, and can administer the medical fluid to the user at a desired administering speed and administering amount by repeatedly carrying out such operation in the set period and interval.

Figure 5:
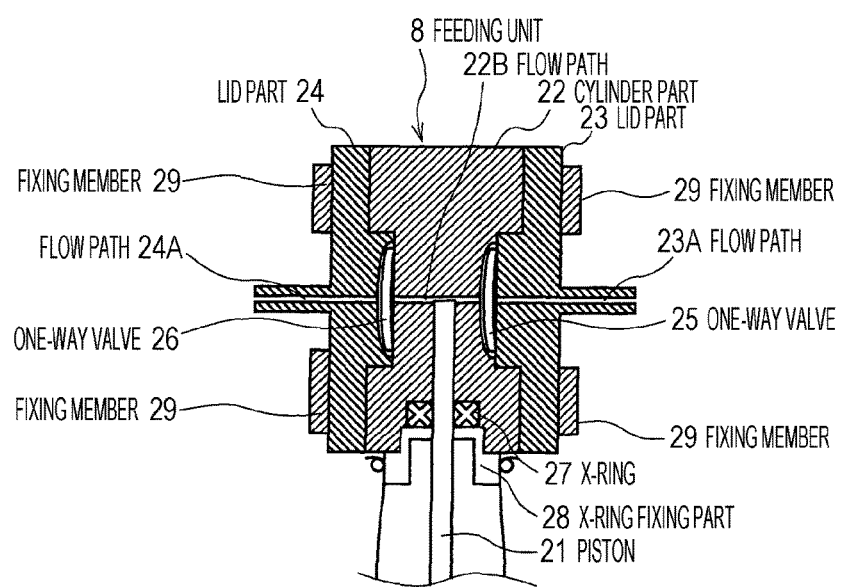
FIG. 5 is a schematic diagram showing a state of a piston moved to a push-in position.

The push-in position is set to the position where the distal end of the piston 21 is on the same plane as the bottom surface of the flow path 22B (surface to which the internal space 22A is connected) or the position in the flow path 22B than the relevant position. In other words, as shown in FIG. 5, when moving the piston 21 to the push-in position, the drive unit 9 moves the piston 21 to the position where the distal end of the piston 21 is on the same plane as the bottom surface of the flow path 22B or the position in the flow path 22B than the relevant position.

If air bubbles exist in the internal space 22A, the feeding unit 8 can push out the air bubbles existing in the internal space 22A into the flow path 22B with the distal end face (upper surface) of the piston 21 when the piston 21 is moved to the push-in position, and hence when the piston 21 is moved to the pull-back position thereafter, the possibility of again taking back the air bubbles into the internal space 22A can be greatly reduced.

On the other hand, in a device in which the distal end of the piston is not moved into the flow path, for example, the air bubbles may attach to the side surface of the cylinder part adjacent to the internal space and the distal end face of the piston, and the air bubbles existing in the internal space may not be pushed out to the flow path when the piston is slidably moved.

In this case, the air bubbles repeatedly expand and contract due to the change in the internal pressure, which changes according to the movement of the piston, whereby the amount of medical fluid taken into the internal space changes and the set amount of medical fluid cannot be fed into the living body. Therefore, in such a case, the medical fluid may not be accurately administered.

On the other hand, the medical fluid administration device 1 pushes out the air bubbles existing in the internal space 22A into the flow path 22B when the piston 21 is moved to the push-in position in the feeding unit 8, and hence when the piston 21 is moved to the pull-back position thereafter, only the medical fluid can be taken into the internal space 22A. Therefore, the medical fluid administration device 1 can accurately administer the medical fluid.

In the medical fluid administration device 1, hydrophilic processing is performed on the distal end face of the piston 21 and the surface of the internal space 22A and the flow path 22B, so that the air bubbles can be further prevented from remaining in the internal space 22A and the flow path 22B.

4. Configuration of Drive Unit

Figure 6A:
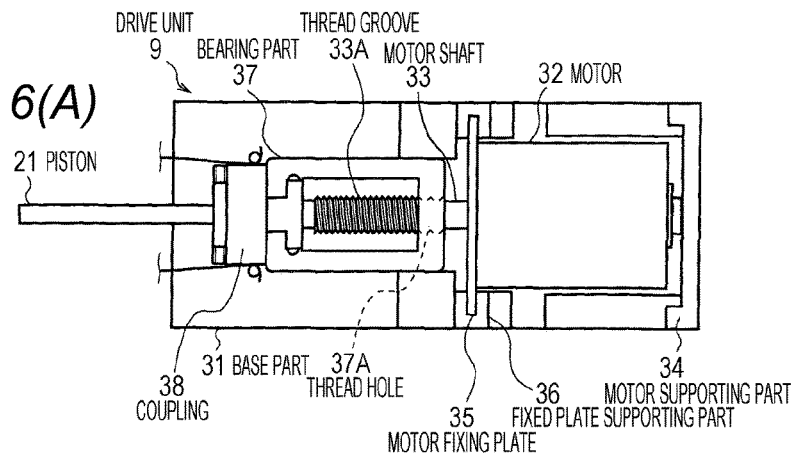
FIGS. 6(A) and 6(B) are schematic diagrams showing a configuration (1) of a drive unit.
Figure 6B:
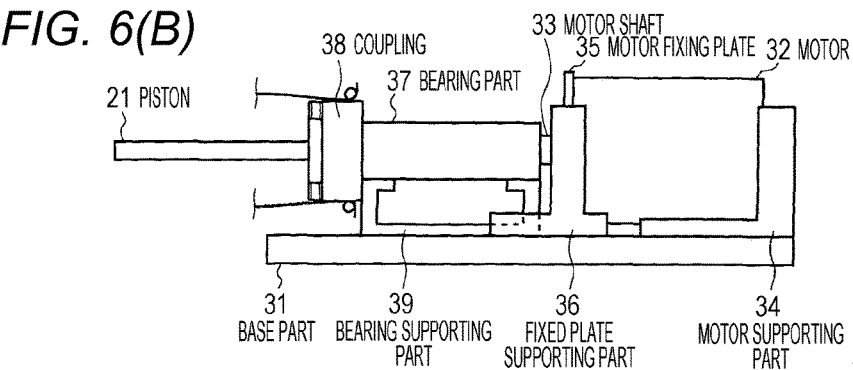

As shown in FIGS. 6(A) and 6(B), the drive unit 9 is configured to include a base part 31, a motor 32, a motor supporting part 34, a motor fixing plate 35, a fixing plate supporting part 36, a bearing part 37, a coupling 38, and a bearing supporting part 39.

The drive unit 9 has each part arranged on the base part 31. The motor 32 is sandwiched by the motor supporting part 34 and the motor fixing plate 35 supported by the fixing plate supporting part 36, and fixed to the base part 31.

The motor 32 includes a motor shaft 33 that projects out from the side surface on the motor fixing plate 35 side. A thread groove 33A is formed on the side surface of the motor shaft 33.

The bearing part 37 is formed to an elongate substantially cuboid shape along the axial direction of the motor 32, and has a hollow interior. The bearing part 37 includes a thread hole 37A at a middle of the side surface corresponding to the short side of the substantially cuboid shape, where the motor shaft 33 of the motor 32 is passed through and arranged in the thread hole 37A so that the thread hole 37A is screw-fitted with the thread groove 33A.

The bearing part 37 has the piston 21 connected coaxially with the motor shaft 33 by way of the coupling 38 to the side surface, which corresponds to the short side of the substantially cuboid shape and faces the side surface formed with the thread hole 37A. The bearing part 37 is supported by the bearing supporting part 39. The coupling 38 is, for example, adapted to alleviate the axial shift of the motor shaft 33 and the piston 21.

Figure 7:
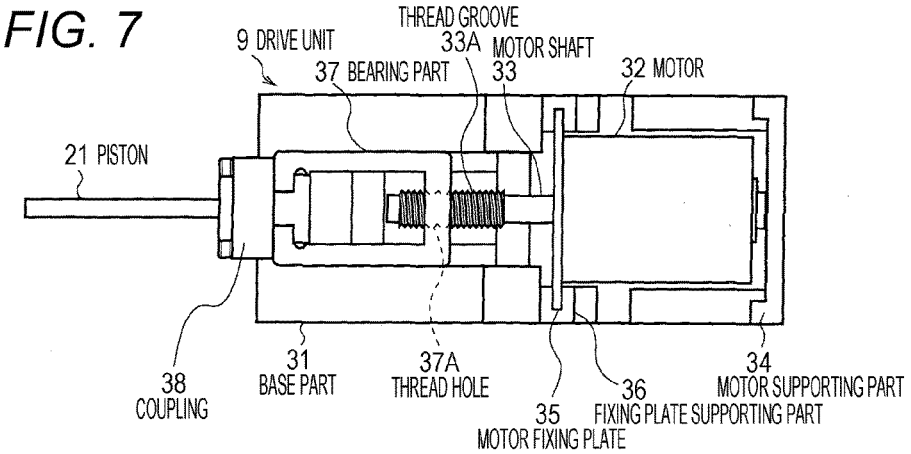
FIG. 7 is a schematic diagram showing a configuration (2) of the drive unit.

As shown in FIGS. 6(A), 6(B) and 7, in the drive unit 9, the motor 32 is driven to rotate the motor shaft 33, and the bearing part 37 screw-fitted to the motor shaft 33 is moved in the axial direction to reciprocate the piston 21 in the axial direction in accordance with the rotation. Thus, the drive unit 9 slidably moves the piston 21 in the internal space 22A of the cylinder part 22. The piston 21 is at the pull-back position in FIGS. 6(A) and 6(B), and the piston 21 is at the push-in position in FIG. 7.

Because the drive unit 9 has the motor shaft 33 of the motor 32 arranged coaxially with the piston 21, the force applied to the bearing part 37 when the motor shaft 33 is rotated, and the force applied to the piston 21 by such force are in the same direction and a loss of thrust force of the piston 21 is eliminated.

Therefore, the drive unit 9 can slidably move the piston 21 at a stable stroke distance in the internal space 22A of the cylinder part 22. Since the drive unit 9 can drive the piston 21 with a smaller force as the loss of the thrust force of the piston 21 is eliminated, the motor 32, the battery, and the like can be made small, and the entire device can be miniaturized. A diamond like carbon may be coated on the side surface of the piston 21 to reduce the sliding movement resistance.

In a device in which the piston and the shaft portion of the motor are not coaxially arranged, the force applied to the bearing part when the shaft portion is rotated and the force applied to the piston by such force become offset, so that the loss of the thrust force of the piston increases and the sliding movement resistance of the bearing part and the piston increases by the offset of the force, whereby not only does the stroke of the piston become unstable but the entire device becomes enlarged.

Figures 8A, 8B:
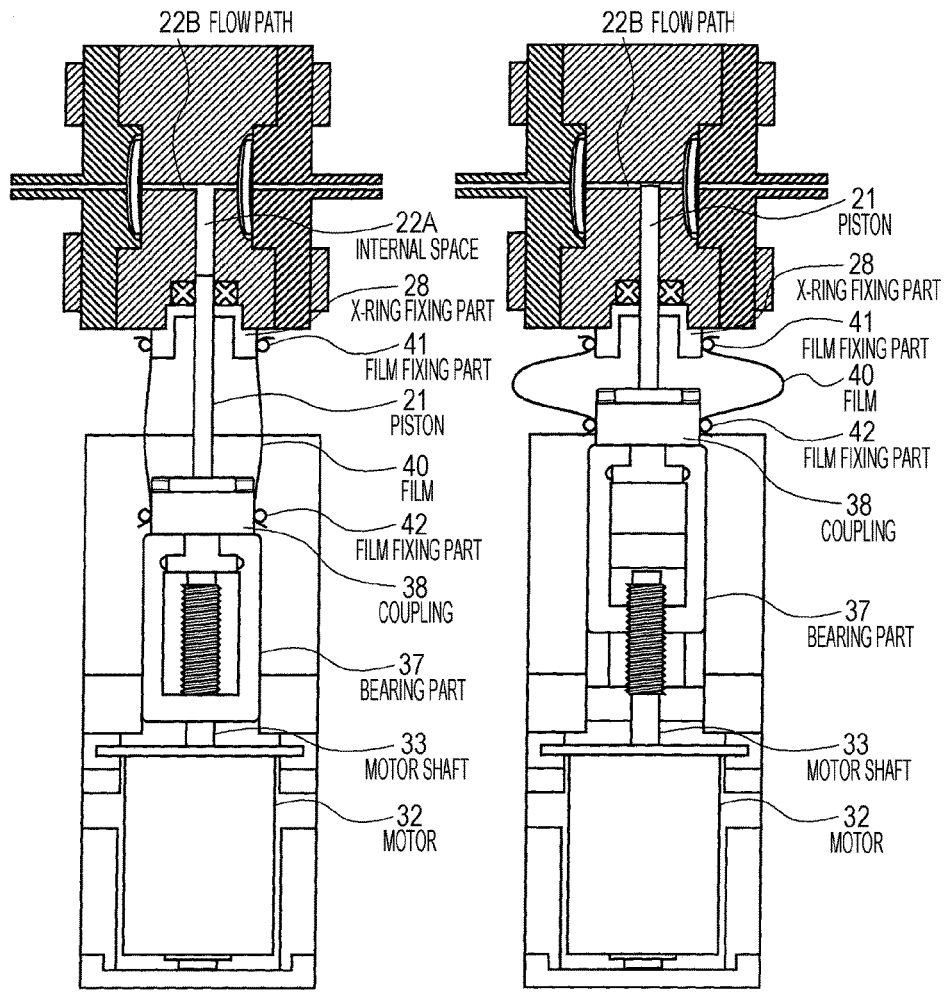
FIGS. 8(A) and 8(B) are schematic diagrams showing a configuration of a feeding unit and the drive unit including a film.

As shown in FIGS. 8(A) and 8(B), in the medical fluid administration device 1, a space between the X-ring fixing part 28 and the coupling 38 is covered with a tube-shaped film 40 having flexibility. Polyethylene, and the like, for example, may be adapted for the material of the film 40.

The film 40 has both ends fixed without a gap across the peripheral direction with respect to the X-ring fixing part 28 and the coupling 38 by film fixing parts 41 and 42 including an O-ring, for example.

Since the film 40 has flexibility, a state in which the piston 21 is covered can be constantly maintained from a state in which the piston 21 is at the pull-back position shown in FIG. 8(A) to a state in which the piston 21 is at the push-in position shown in FIG. 8(B).

Therefore, in the medical fluid administration device 1, the piston 21 can be slidably moved in the internal space 22A of the cylinder part 22 without touching the air outside the film 40. Thus, the medical fluid administration device 1 can further maintain the cleanliness of the piston 21 that enters the internal space 22A.

5. Configuration of Puncture Mechanism

Figure 9:
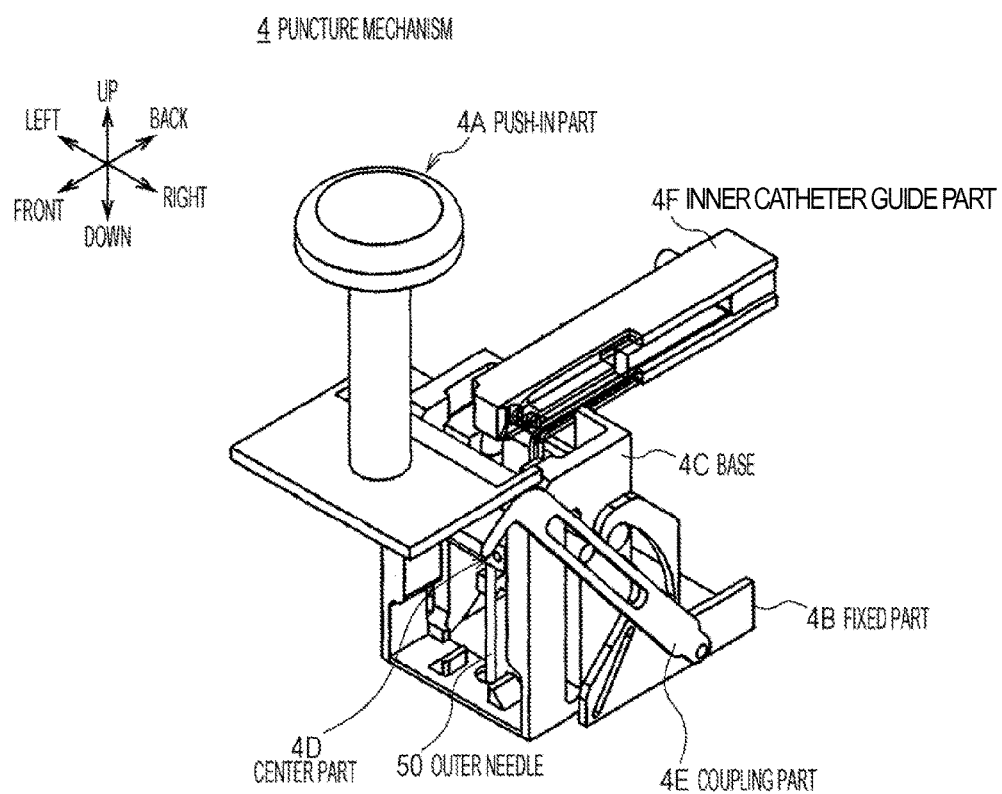
FIG. 9 is a schematic diagram showing a configuration of a puncture mechanism.
Figure 10:
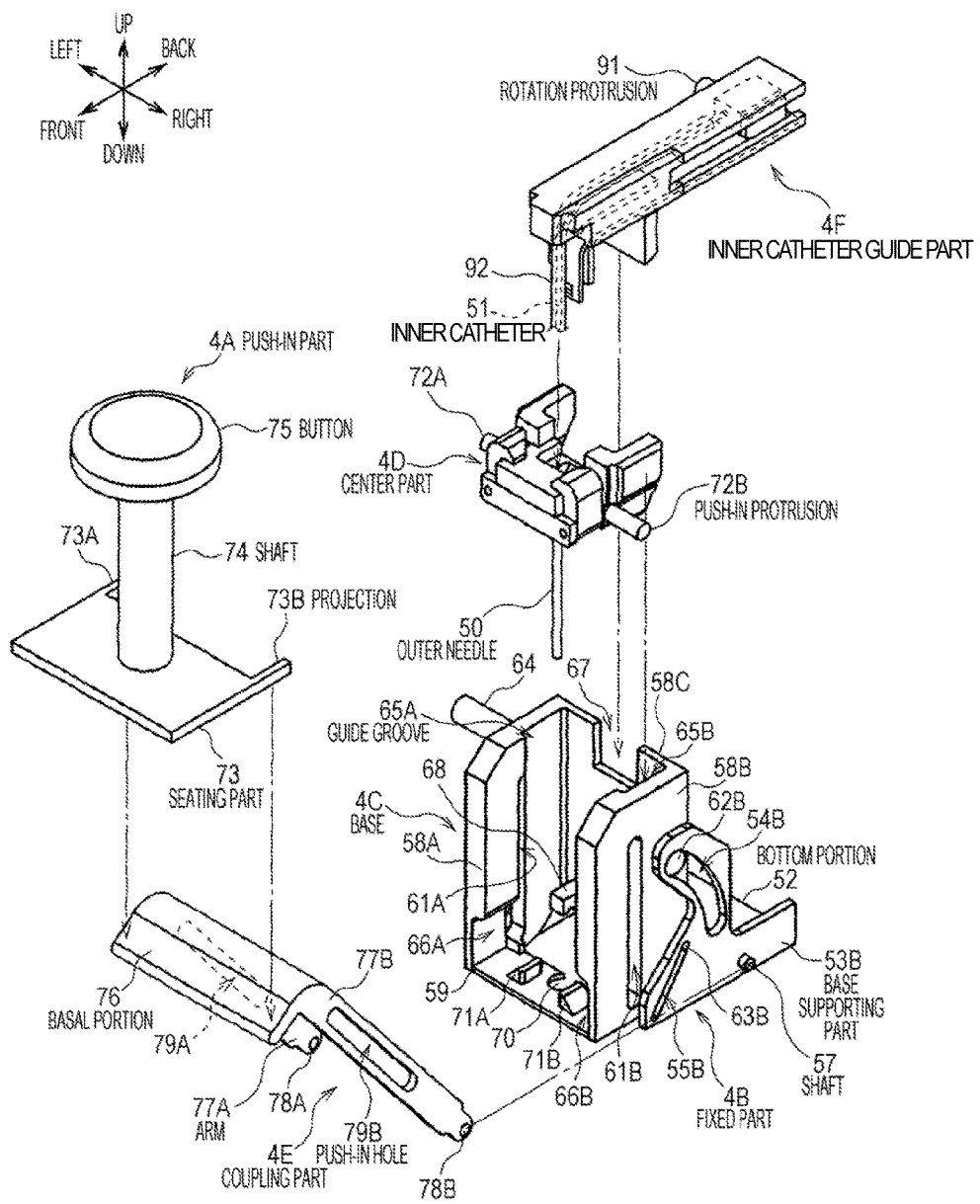
FIG. 10 is a schematic diagram showing an exploded perspective view of the puncture mechanism.

A configuration of the puncture mechanism 4 will now be described in detail. As shown in FIGS. 9 and 10, the puncture mechanism 4 mainly includes the push-in part 4A, a fixed part 4B fixed to the front end side interior of the bottom surface 2A of the lower housing unit 2, a base 4C attached to the fixed part 4B in a freely tilting manner, a center part 4D that is slidable on the inner side of the base 4C according to the push-in operation of the push-in part 4A and that includes the outer needle 50, a coupling part 4E that couples the push-in part 4A and the center part 4D and transmits the force with which the push-in part 4A is pushed in to the center part 4D to slide the center part 4D, and an inner catheter guide part 4F that guides the inner catheter 51 from the back of the base 4C to the inner side of the base 4C.

As will be specifically described below, the puncture mechanism 4 can adjust the puncture angle of the puncture needle (outer needle 50 and inner catheter 51) in a range of 90 degrees to 30 degrees, for example, by tilting the base 4C with respect to the fixed part 4B by the puncture angle adjustment mechanism 5.

The puncture mechanism 4 itself carries out a similar operation regardless of the degree of the puncture angle, and hence the puncture mechanism 4 will be described in detail using a case in which the puncture angle is 90 degrees, that is, a case in which the angle of the puncture needle (outer needle 50 and inner catheter 51) with respect to the attachment surface of the lower housing unit 2 is a right angle, by way of example.

Figure 11:
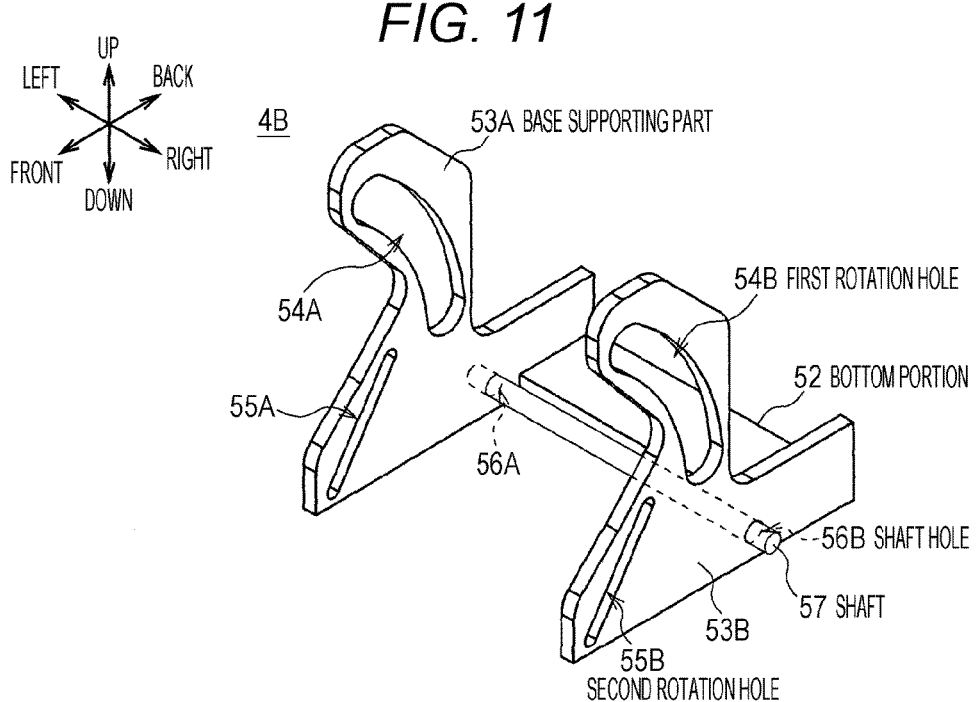
FIG. 11 is a schematic diagram showing a configuration of a fixed part.

As shown in FIGS. 10 and 11, the fixed part 4B is configured by a rectangular plate shaped bottom portion 52 that is parallel to the bottom surface 2A of the lower housing unit 2 and that is long in the left and right direction, and a pair of base supporting portions 53A and 53B having a substantially L-shaped plate form arranged at both left and right ends of the bottom portion 52 so as to be orthogonal with the bottom surface 2A of the lower housing unit 2.

The base supporting portions 53A and 53B have holes (hereinafter also referred to as first rotation holes) 54A and 54B, extending in a curved form from the upper end toward the middle, formed at the side surfaces. On the side surfaces of the base supporting portions 53A and 53B are also formed holes (hereinafter referred to as second rotation holes) 55A and 55B extending in a linear form from the lower end to the middle on the front side of the first rotation holes 54A and 54B.

The first rotation holes 54A and 54B have a curve shape bulged toward the back side, and the second rotation holes 55A and 55B are narrower than the first rotation holes 54A and 54B and have a linear shape inclined so that the upper end is positioned on the back side than the lower end.

Furthermore, circular holes (hereinafter also referred to as shaft holes) 56A and 56B are formed at substantially the middle of the lower end on the side surfaces of the base supporting portions 53A and 53B, and a shaft 57 is fitted into the shaft holes 56A and 56B.

The shaft 57 is a part of the coupling part 4E, as will be described in detail below, and the length thereof is selected such that the left and right distal end portions project out to the outer side from the shaft holes 56A and 56B when fitted into the shaft holes 56A and 56B.

The base supporting portions 53A and 53B have the back part of the lower end of the respective inner side surfaces integrally molded with the bottom portion 52 so as to be connected by the bottom portion 52.

The interval of the base supporting portions 53A and 53B is substantially equal to the left and right width of the base 4C.

Figure 12:
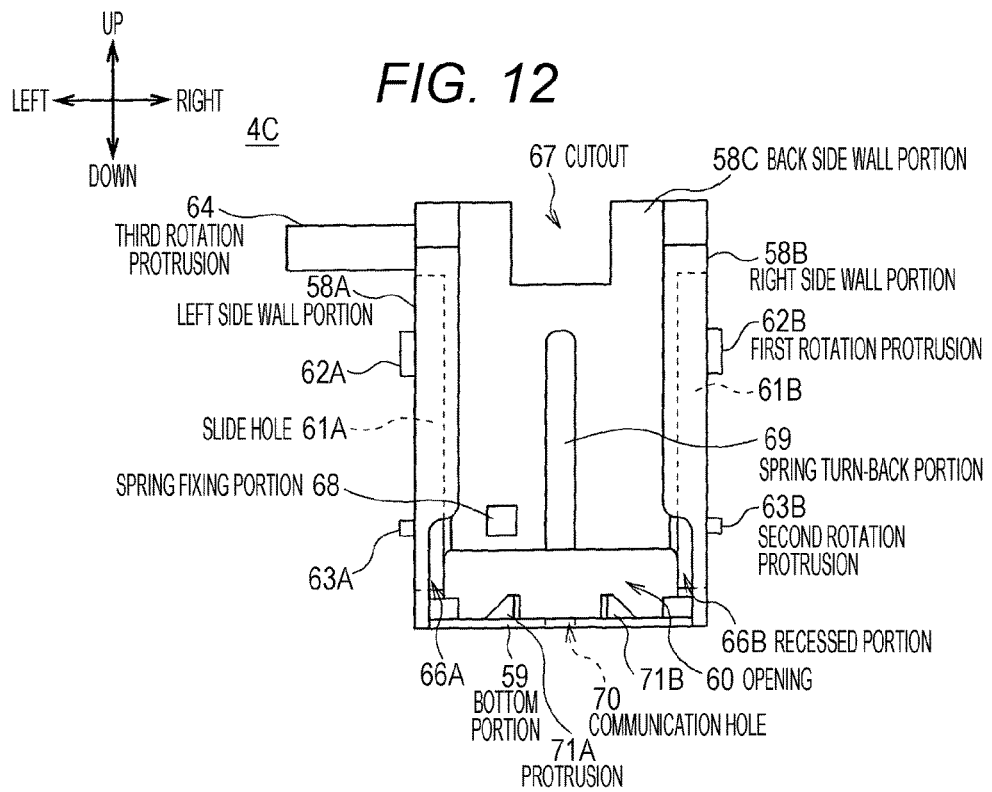
FIG. 12 is a schematic diagram showing a configuration of a base.

As shown in FIGS. 10 and 12, the base 4C includes three wall portions 58A, 58B, 58C, on the left, the right and the back side. The left side wall portion 58A and the right side wall portion 58B are longer toward the lower side than the back side wall portion 58C, where the front part of the lower end has a linear shape parallel in the front and back direction whereas the back part has a curved shape as if the corner is rounded (see FIG. 15(A)).

Furthermore, the left side wall portion 58A and the right side wall portion 58B include a plate-shaped bottom portion 59 so as to connect the front parts (linear portions) of the respective lower ends.

At the back part of the lower end of the base 4C, an opening 60 is formed by the back end of the bottom portion 59, the back parts (portion of curved shape) of the lower ends of the left side wall portion 58A and the right side wall portion 58B, and the lower end of the back side wall portion 58C.

Furthermore, holes (slide holes) 61A and 61B linearly extending in the up and down direction from the middle of the upper end toward the middle of the lower end are formed on the side surfaces of the left side wall portion 58A and the right side wall portion 58B. The role of the slide holes 61A and 61B will be described below.

On the outer side surfaces of the left side wall portion 58A and the right side wall portion 58B, circular column shaped protrusions (hereinafter also referred to as first rotation protrusions) 62A and 62B to be fitted into the first rotation holes 54A and 54B of the fixed part 4B are arranged in a projecting manner at positions slightly on the upper side of the middle on the back side than the slide holes 61A and 61B.

On the outer side surfaces of the left side wall portion 58A and the right side wall portion 58B, circular column shaped protrusions (hereinafter also referred to as second rotation protrusions) 63A and 63B to be fitted into the second rotation holes 55A and 55B of the fixed part 4B are arranged in a projecting manner at positions slightly on the upper side than the lower end of the back side wall portion 58C at the lower side than the first rotation protrusions 62A and 62B.

The base 4C is sandwiched between the base supporting portions 53A and 53B of the fixed part 4B, and is attached in a freely tilting manner with respect to the fixed part 4B by fitting the first rotation protrusions 62A and 62B into the first rotation holes 54A and 54B of the fixed part 4B, and fitting the second rotation protrusions 63A and 63B into the second rotation holes 55A and 55B of the fixed part 4B.

As will be specifically described in detail below, the puncture angle becomes a maximum of 90 degrees when the first rotation protrusions 62A and 62B of the base 4C are positioned at the upper ends of the first rotation holes 54A and 54B of the fixed part 4B, and the second rotation protrusions 63A and 63B are positioned at the upper ends of the second rotation holes 55A and 55B of the fixed part 4B.

The base 4C is tilted so as to fall backward in a manner the first rotation protrusions 62A and 62B of the base 4C are moved toward the lower end side of the first rotation holes 54A and 54B of the fixed part 4B, and the second rotation protrusions 63A and 63B are moved toward the lower end side of the second rotation holes 55A and 55B of the fixed part 4B, thus reducing the puncture angle.

When the first rotation protrusions 62A and 62B of the base 4C reach the lower ends of the first rotation holes 54A and 54B of the fixed part 4B, and the second rotation protrusions 63A and 63B reach the lower ends of the second rotation holes 55A and 55B of the fixed part 4B, the puncture angle becomes a minimum of 30 degrees.

Furthermore, a circular column shaped protrusion (hereinafter also referred to as third rotation protrusion) 64, which is to be fitted into the hole (to be described below) of the dial 5A of the puncture angle adjustment mechanism 5, is arranged in a projecting manner at the middle of the upper end on the outer side surface of the left side wall portion 58A of the base 4C.

Furthermore, a groove 65A and a groove 65B extending from the lower end to the upper end are arranged at positions closer to the back side on the respective inner side surfaces of the left side wall portion 58A and the right side wall portion 58B.

The grooves 65A and 65B are grooves that act as guides when the center part 4D is slid along the inner wall of the base 4C, and are hereinafter referred to as guide grooves 65A and 65B.

Recessed portions 66A and 66B are arranged at the lower ends on the front side than the guide grooves 65A and 65B on the respective inner side surfaces of the left side wall portion 58A and the right side wall portion 58B. The role of the recessed portions 66A and 66B will be described below.

Furthermore, a horseshoe shaped cutout 67, to which the inner catheter guide part 4F is fitted, is formed at the middle of the upper end of the back side wall portion 58C.

Furthermore, a spring fixing portion 68 for fixing one end of a coil spring (to be described below) is arranged in a projecting manner at a position closer to the left at the lower end on the inner side surface of the back side wall portion 58C.

A spring turn-back portion 69 (FIG. 12) extending from the middle of the lower end to the position (position closer to the upper end at the middle) immediately below the cutout 67 is arranged in a projecting manner on the inner side surface of the back side wall portion 58C. The spring turn-back portion 69 is provided to turn back the other end side of the coil spring (not shown), which one end is fixed to the spring fixing portion 68. The coil spring will be described in detail below, but is provided to pull back only the outer needle into the medical fluid administration device 1 after puncturing the puncture needle including the outer needle made of metal and the inner catheter made of resin into the body of the user.

A communication hole 70 that communicates with the puncture needle hole 2C formed at the bottom surface 2A of the lower housing unit 2 is arranged at a position slightly on the back side of the middle in the bottom portion 59, and two protrusions 71A and 71B are arranged in a projecting manner with a predetermined spacing to the left and right of the communication hole 70. The communication hole 70 has a C-shape with the back end side opened, and is connected to the opening 60.

The center part 4D will be described in detail below, but circular column shaped protrusions 72A and 72B projecting out to the outer side are arranged on both left and right side surface portions, as shown in FIG. 10. The protrusions 72A and 72B are referred to as push-in protrusions 72A and 72B.

The center part 4D is fitted into the inner side of the base 4C such that the push-in protrusions 72A and 72B are fitted into the slide holes 61A and 61B of the base 4C, and is slidable in the up and down direction along the slide holes 61A and 61B and the guide grooves 65A and 65B on the inner side of the base 4C.

The length of the push-in protrusions 72A and 72B of the center part 4D is selected such that the left and right distal end portions project out to the outer side from the slide holes 61A and 61B when the push-in protrusions 72A and 72B of the center part 4D are fitted into the slide holes 61A and 61B. The role of the push-in protrusions 72A and 72B will be described below.

As shown in FIG. 10, the push-in part 4A is configured by a plate-shaped seating part 73 parallel to the bottom surface 2A of the lower housing unit 2, a shaft 74 perpendicularly arranged at the middle of the upper surface of the seating part 73, and a button 75 arranged at the upper end of the shaft 74.

The seating part 73 has projections 73A and 73B, which project out toward the back side, arranged at both left and right ends of the back end portion, and the projections 73A and 73B are brought into contact with the coupling part 4E, as will be described in detail below.

Although the illustration will be omitted, the push-in part 4A can be moved in the up and down direction in the interior of the medical fluid administration device 1 along the guide portion arranged in a projecting manner in the interior of the front end side of the bottom surface 2A of the lower housing unit 2.

The coupling part 4E is configured by a rectangular plate shaped basal portion 76 that is long in the left and right direction, and a pair of arms 77A and 77B extending in a direction orthogonal to the basal portion 76 from both left and right ends of the basal portion 76.

The interval of the arms 77A and 77B is substantially equal to the left and right width of the fixed part 4B.

The arms 77A and 77B have circular holes 78A and 78B formed at the distal end thereof. The arms 77A and 77B include holes 79A and 79B linearly extending from a root portion toward the middle. The holes 78A and 78B are referred to as shaft holes 78A and 78B, and the holes 79A and 79B are referred to as push-in holes 79A and 79B.

The coupling part 4E is attached in a freely rotating manner to the fixed part 4B by fixing the distal end portions of the shaft 57 (portions projecting out to the outer side from the shaft holes 56A and 56B) fitted into the shaft holes 56A and 56B of the fixed part 4B to the shaft holes 78A and 78B of the arms 77A and 77B.

The coupling part 4E has the push-in holes 79A and 79B of the arms 77A and 77B fitted into the distal end portions (portions projecting out to the outer side from the slide holes 61A and 61B of the base 4C) of the push-in protrusions 72A and 72B of the center part 4D fitted to the inner side of the base 4C.

Furthermore, in this case, the coupling part 4E has the basal portion 76 positioned below the seating part 73 of the push-in part 4A, and the projections 73A and 73B of the push-in part 4A are brought into contact with both left and right end portions of the upper surface of the basal portion 76.

The coupling part 4E is connected to both the center part 4D fitted into the base 4C and the push-in part 4A, so that the center part 4D and the push-in part 4A are coupled by way of the coupling part 4E.

Actually, when the push-in part 4A is pushed down and slid toward the lower side, the basal portion 76 is pushed downward, so that the coupling part 4E is rotated to lower the basal portion 76 with the shaft 57 as a rotation shaft.

In this case, the push-in protrusions 72A and 72B of the center part 4D fitted to both the slide holes 61A and 61B of the base 4C and the push-in holes 79A and 79B of the arms 77A and 77B are slid toward the lower side in the slide holes 61A and 61B while sliding toward the distal end side in the push-in holes 79A and 79B with the rotation of the coupling part 4E. As a result, the center part 4D is slid toward the lower side on the inner side of the base 4C.

Thus, the coupling part 4E is rotated by the force at which the push-in part 4A is pushed in, thus transmitting such force to the center part 4D and sliding the center part 4D.

Figure 13:
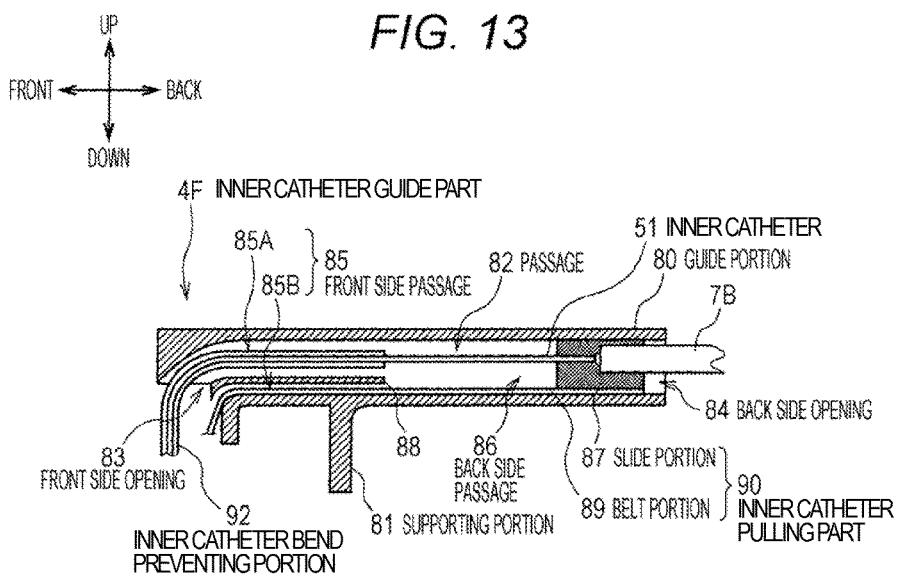
FIG. 13 is a schematic diagram showing a configuration of an inner catheter guide part.

As shown in FIGS. 10 and 13, the inner catheter guide part 4F is configured by a substantially column shaped guide portion 80 extending in the front and back direction, and a plate shaped supporting portion 81 arranged in a projecting manner at a position closer to the front side than the middle of the lower surface of the guide portion 80.

The guide portion 80 interiorly includes a passage 82 that extends in the front and back direction. The guide portion 80 has a shape in which the front end portion of the lower surface is bent toward the lower side, where a downward opening 83 connecting to the passage 82 is arranged on the front side of the bent portion. The guide portion 80 also includes a backward opening 84 connecting to the passage 82 at the back surface.

The opening 83 on the front side is referred to as front side opening 83, and the opening 84 on the back side is referred to as back side opening 84.

The inner catheter guide part 4F is attached to the base 4C by fitting the guide portion 80 into the cutout 67 of the base 4C with the front end portion of the guide portion 80 projecting out toward the front side than the back side wall portion 58C of the base 4C.

In this case, the supporting portion 81 of the inner catheter guide part 4F makes contact with the outer side surface of the back side wall portion 58C of the base 4C thus supporting the guide portion 80 so as to be orthogonal to the back side wall portion 58C.

When the inner catheter guide part 4F is attached to the base 4C in such manner, the front side opening 83 is positioned on the front side than the back side wall portion 58C and is positioned immediately above the outer needle 50 of the center part 4D attached to the base 4C.

In the passage 82 of the inner catheter guide part 4F, the portion from the back side opening 84 to the vicinity of the front end is linear, and the portion further therefrom to the front side opening 83 is curved downward so as to draw a smooth curve.

The passage 82 includes a front side passage 85, which is the portion on the front side than the middle, and a back side passage 86, which is the portion on the back side than the middle, where the back side passage 86 is one passage whereas the front side passage 85 is divided into two passages 85A and 85B on the top and bottom.

The passage 85A on the upper side of the front side passage 85 is referred to as an upper side passage 85A and the passage 85B on the lower side is referred to as a lower side passage 85B. The upper side passage 85A and the lower side passage 85B have distal ends connected to the front side opening 83 and the back ends connected to the back side passage 86.

The upper side passage 85A is a passage through which the inner catheter 51 passes, and is a passage thicker than the lower side passage 85B.

The inner catheter 51 is passed through the back side passage 86 and the upper side passage 85A, bent downward at the front end of the upper side passage 85A, extended downward from the front side opening 83, and inserted into the outer needle 50 of the center part 4D.

A slide portion 87 that is slidable in the back side passage 86 and that connects and fixes the back end of the inner catheter 51 and the front end of the feeding tube 7B connected to the medical fluid storage unit 6 is arranged in the passage 82.

Actually, when the slide portion 87 is slid toward the front side in the back side passage 86 of the inner catheter guide part 4F, the inner catheter 51 is moved toward the front side in the passage 82 accompanying therewith, and is pushed out toward the lower side from the front side opening 83.

The slide portion 87 is prevented from sliding any further toward the front side when the front end makes contact with the back end of a boundary portion 88 between the upper side passage 85A and the lower side passage 85B.

The slide portion 87 has the lower end fixed to the back end of a belt portion 89 including a belt made of metal or resin.

The belt portion 89 is passed through the back side passage 86 and the lower side passage 85B, bent downward at the front end of the lower side passage 85B, extended downward from the front side opening 83 and fixed to the center part 4D at the distal end.

The center part 4D and the slide portion 87 are coupled by the belt portion 89, so that the slide portion 87 slides in cooperation with the sliding of the center part 4D.

Actually, when the center part 4D is slid toward the lower side by the push-in operation on the push-in part 4A, the slide portion 87 is slid toward the front side by the belt portion 89 and the inner catheter 51 is also moved.

Thus, the belt portion 89 and the slide portion 87 function as an inner catheter pulling part 90 that pulls the inner catheter 51 with the sliding of the center part 4D by the push-in operation on the push-in part 4A.

Thus, when the center part 4D is slid toward the lower side, the outer needle 50, which is a part of the center part 4D, and the inner catheter 51 having the distal end inserted into the outer needle 50 are both moved.

As shown in FIG. 10, the inner catheter guide part 4F has a circular column shaped protrusion (also referred to as a rotation protrusion) 91 arranged in a projecting manner at a predetermined position on the left side surface. The role of the rotation protrusion 91 will be described below. Furthermore, the inner catheter guide part 4F is configured such that the front side of the right side surface is detachable, so that the inside can be easily checked by detaching the front side of the right side surface.

The inner catheter 51 guided by the inner catheter guide part 4F has the portion on the back end side than the portion inserted to the outer needle 50 of the center part 4D inserted into a tubular inner catheter bend preventing portion 92 having an inner diameter insertable into the upper side passage 85A and greater than the outer diameter of the inner catheter 51.

As will be described in detail below, the inner catheter bend preventing portion 92 is a member made of resin that prevents the inner catheter 51 from being bent between the center part 4D and the front side opening 83 of the inner catheter guide part 4F.

Figure 14:
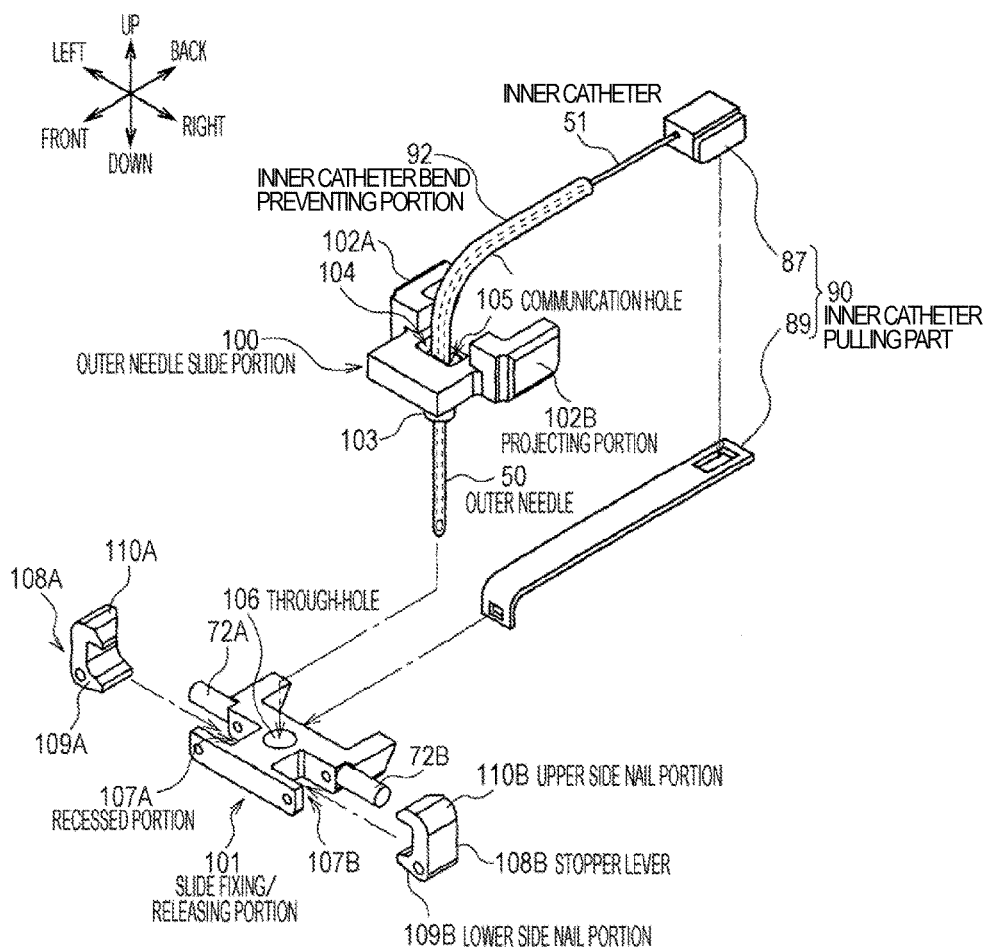
FIG. 14 is a schematic diagram showing a configuration of a center part.

The center part 4D will be described in detail below. As shown in FIG. 14, the center part 4D mainly includes an outer needle slide portion 100 including the outer needle 50 of the puncture needle, and a slide fixing/releasing portion 101 for fixing or releasing the outer needle slide portion 100.

The outer needle slide portion 100 is provided to overlap on the slide fixing/releasing portion 101, where the front part has a square plate shape, the back part has a substantially horseshoe shape opened toward the back side, and the left and right side surface parts on the back part respectively have a shape extending toward the upper side.

The outer needle slide portion 100 has the lower part of the back end face formed to an inclined surface inclined as if the corner is cut off.

Furthermore, the outer needle slide portion 100 has projecting portions 102A and 102B formed at the left and right side surface parts on the back side.

Each of the projecting portions 102A and 102B is a portion to be fitted into the guide grooves 65A and 65B of the base 4C, so that the outer needle slide portion 100 can be slid in the up and down direction along the guide grooves 65A and 65B of the base 4C.

In the outer needle slide portion 100, a tubular protrusion 103 that is thicker than the outer needle 50 and that has substantially the same diameter as the communication hole 70 formed at the bottom portion 59 of the base 4C is arranged in a projecting manner toward the lower side at the middle of the bottom surface.

The outer needle 50 made of metal is extended toward the lower side from the lower end of the protrusion 103. The outer needle 50 is a hollow tubular needle, and for example, has a size of 8 mm in length, 0.4 mm in outer diameter, and 0.2 mm in inner diameter.

Furthermore, a recessed portion 104 is formed at the central portion of the upper surface of the outer needle slide portion 100, and a communication hole 105 that communicates with the outer needle 50 is formed at the middle of the recessed portion 104.

The inner catheter 51 extending toward the lower side from the front side opening 83 of the inner catheter guide part 4F is inserted into the outer needle 50 through the communication hole 105.

Moreover, the distal end of the inner catheter bend preventing portion 92 described above is attached to the recessed portion 104. Thus, the inner catheter 51 has the portion on the back end side than the portion inserted into the outer needle 50 inserted in the inner catheter bend preventing portion 92.

The outer needle slide portion 100 having such configuration is slidable in the up and down direction between the inner catheter guide part 4F attached to the upper end of the base 4C and the bottom portion 59 on the inner side of the base 4C.

Figure 15A:
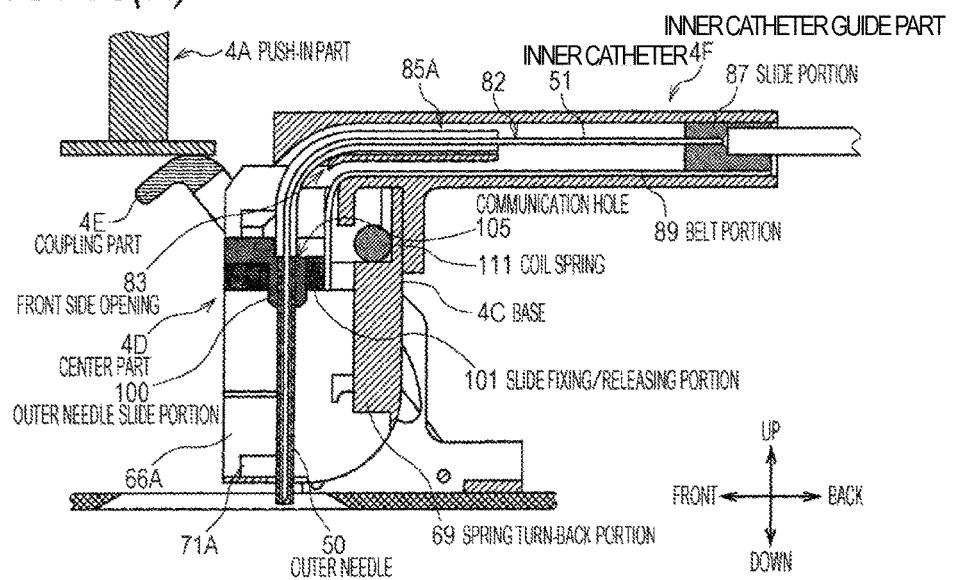
FIGS. 15(A) and 15(B) are schematic diagrams involved in the description of the operation of the puncture mechanism.

Actually, when the outer needle slide portion 100 is positioned at the most upper side, the communication hole 105 is positioned immediately below the front side opening 83 of the inner catheter guide part 4F, as shown in FIG. 15(A).

In this case, the inner catheter bend preventing portion 92 is in a state of having substantially a half accommodated in the upper side passage 85A of the inner catheter guide part 4F.

Figure 16A:
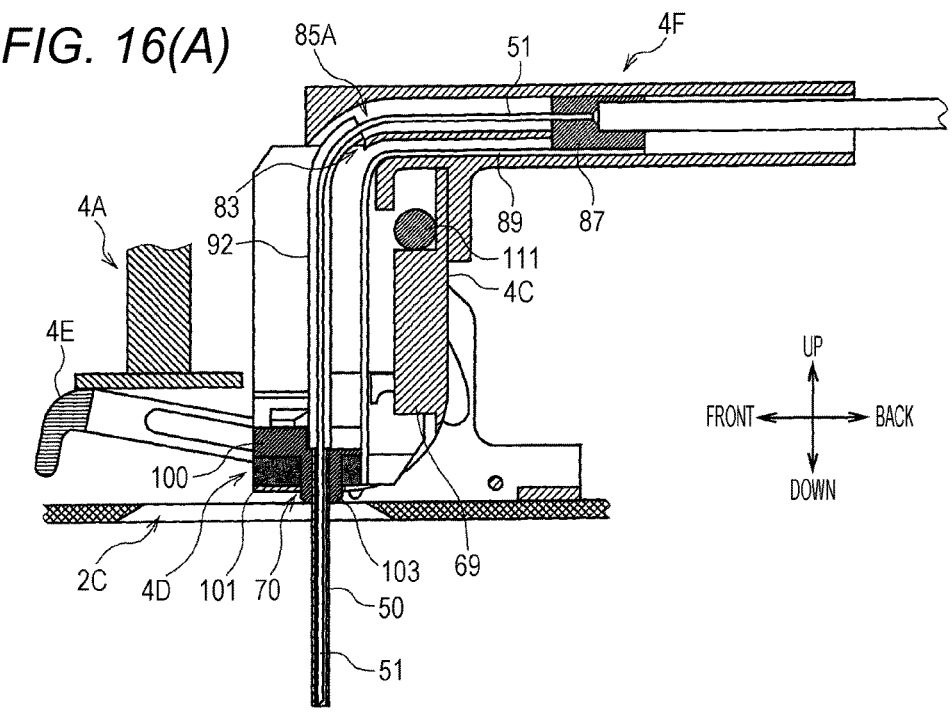
FIGS. 16(A) and 16(B) are schematic diagrams involved in the description of the operation of the puncture mechanism.

Furthermore, when the outer needle slide portion 100 is positioned at the most lower side, the protrusion 103 is fitted into the communication hole 70 of the bottom portion 59 of the base 4C, as shown in FIG. 16(A).

In this case, the protrusion 103 has the distal end portion slightly projecting out to the lower side from the communication hole 70.

In this case, the inner catheter bend preventing portion 92 has the back end portion remaining at the front end part of the upper side passage 85A of the inner catheter guide part 4F, and the remaining portion exposed to the outside of the upper side passage 85A.

As shown in FIG. 14, the slide fixing/releasing portion 101 has a plate shape in which the front side has a substantially T-shape and the back side has a substantially horseshoe shape opened toward the back side.

The slide fixing/releasing portion 101 has the distal end of the belt portion 89 of the inner catheter pulling part 90 described above fixed to a predetermined position at the back part. In other words, the slide fixing/releasing portion 101 is fixed to the inner catheter pulling part 90.

The slide fixing/releasing portion 101 has a through-hole 106, which passes through in the up and down direction to pass the protrusion 103 and the outer needle 50 arranged at the bottom surface of the outer needle slide portion 100, at the central portion.

Furthermore, the slide fixing/releasing portion 101 has recessed portions 107A and 107B formed at the position closer to the front side of the left and right side surfaces, and the push-in protrusions 72A and 72B, described above, formed at the central portion on the left and right side surfaces.

Furthermore, the left and right recessed portions 107A and 107B have stopper levers 108A and 108B having a horseshoe-shaped cross-section attached in a freely rotating manner so as to face the internal opening, respectively.

Specifically, each of the stopper levers 108A and 108B has lower side nail portions 109A and 109B pivotally supported at each of the recessed portions 107A and 107B through a shaft (not shown).

Thus, the stopper levers 108A and 108B can rotate in a direction of approaching and in a direction of separating the upper side nail portions 110A and 110B with the shaft (not shown) as an axis.

The rotation of the upper side nail portions 110A and 110B in the direction of approaching means closing the stopper levers 108A and 108B, and the rotation in the direction of separating means opening the stopper levers 108A and 108B.

When closed, the stopper levers 108A and 108B have the upper side nail portions 110A and 110B positioned on the upper side by a predetermined length from the upper surface of the slide fixing/releasing portion 101.

When closed, the stopper levers 108A and 108B are accommodated in a stepless manner with the left and right side surfaces of the slide fixing/releasing portion 101.

Moreover, the thickness of the slide fixing/releasing portion 101 is formed thinner than the projection amount of the protrusion 103 of the outer needle slide portion 100, so that the distal end portion of the protrusion 103 projects out to the lower side from the through-hole 106 of the slide fixing/releasing portion 101 with the outer needle 50 when overlapped.

The distal end portion of the protrusion 103 projected out to the lower side is the portion to be fitted into the communication hole 70 of the bottom portion 59 of the base 4C.

Figure 15B:
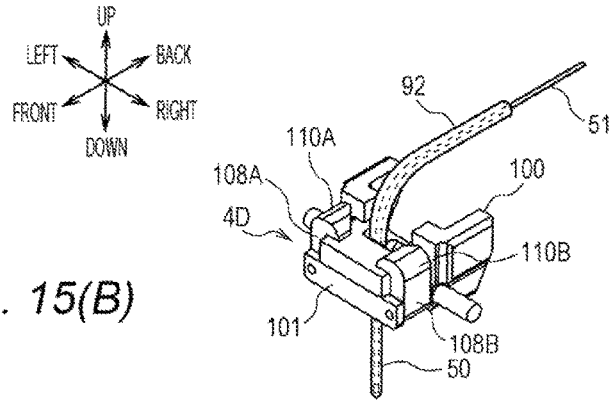

Furthermore, when the left and right stopper levers 108A and 108B are closed with the outer needle slide portion 100 overlapped on the slide fixing/releasing portion 101, the outer needle slide portion 100 is sandwiched between the upper side nail portions 110A and 110B of the left and right stopper levers 108A and 108B and the upper surface of the slide fixing/releasing portion 101, as shown in FIG. 15(B), so that the outer needle slide portion 100 is fixed to the slide fixing/releasing portion 101.

Figure 16B:
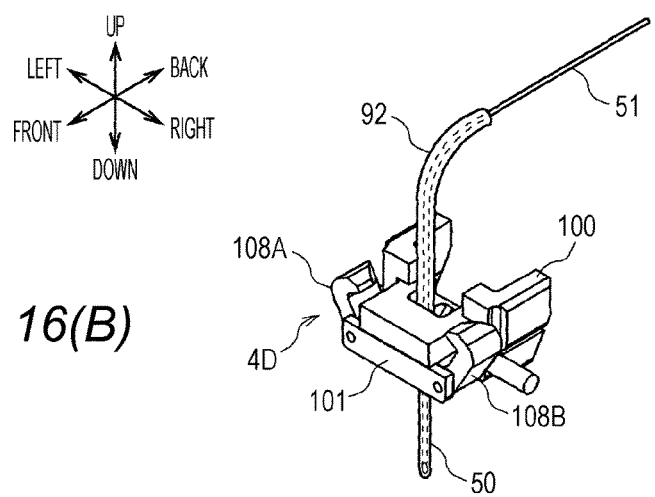

When the left and right stopper levers 108A and 108B are opened from such state, as shown in FIG. 16(B), the fixing of the slide fixing/releasing portion 101 and the outer needle slide portion 100 is released.

Moreover, the slide fixing/releasing portion 101 also has the back end face formed to an inclined surface inclined as if the corner on the lower side is cut off.

The center part 4D configured as above is fitted to the inner side of the base 4C by fitting the projecting portions 102A and 102B of the outer needle slide portion 100 into the guide grooves 65A and 65B on the inner side of the base 4C and fitting the push-in protrusions 72A and 72B of the slide fixing/releasing portion 101 into the slide holes 61A and 61B of the base 4C with the outer needle slide portion 100 overlapped on the slide fixing/releasing portion 101 and the inner catheter 51 inserted into the outer needle 50 of the outer needle slide portion 100.

As shown in FIG. 15(A), the center part 4D is arranged at the upper end on the inner side of the base 4C as an initial position.

In this case, the center part 4D has the communication hole 105 of the outer needle slide portion 100 positioned immediately below the front side opening 83 of the inner catheter guide part 4F, and the distal end portion of the inner catheter 51 bent downward by the inner catheter guide part 4F inserted into the outer needle 50 through the communication hole 105.

In this case, the entire outer needle 50 is accommodated in the medical fluid administration device 1, and the projection amount from the medical fluid administration device 1 of the push-in part 4A is a maximum.

Furthermore, in this case, the center part 4D has the left and right stopper levers 108A and 108B pushed toward the inner side by the left side wall portion 58A and the right side wall portion 58B of the base 4C, so that the stopper levers 108A and 108B are in a closed state, as shown in FIG. 15(B).

In other words, in this case, the center part 4D fixes the outer needle slide portion 100 to the slide fixing/releasing portion 101.

Figure 17A:
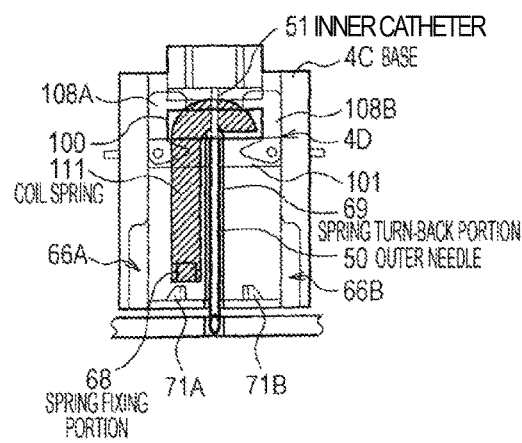
FIGS. 17(A) to 17(D) are schematic diagrams involved in the description of the operation of the puncture mechanism.

Furthermore, when at the initial position, the center part 4D is positioned on the front side of the upper end of the spring turn-back portion 69 arranged at the back side wall portion 58C of the base 4C, as shown in FIG. 17(A).

The coil spring 111 having one end fixed to the spring fixing portion 68 arranged at the lower end closer to the left of the back side wall portion 58C of the base 4C has the other end fixed to a predetermined position closer to the right at the back part of the outer needle slide portion 100 with the other end side bent downward by the spring turn-back portion 69 to a J shape.

The coil spring 111 in this case has a natural length that is not extended nor contracted. From such state, the user pushes the push-in part 4A into the medical fluid administration device 1.

Figure 17B:
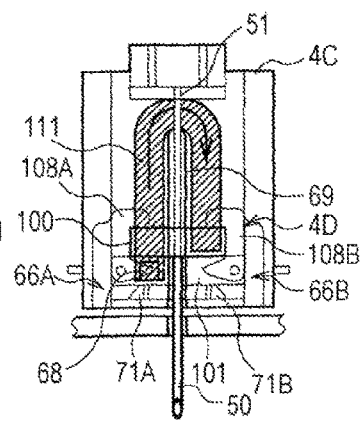

Then, as shown in FIG. 17(B), the force of pushing in the push-in part 4A is transmitted to the center part 4D through the coupling part 4E, so that the center part 4D is slid toward the lower side on the inner side of the base 4C. Furthermore, as the outer needle slide portion 100 of the center part 4D is slid toward the lower side, the entire coil spring 111 is extended to deform from the J shape to the U shape.

6. Operation of Puncture Mechanism

The operation of the puncture mechanism 4 of when actually puncturing the outer needle 50 and the inner catheter 51, which are the puncture needle, into the body of the user will now be described in detail. A case in which the puncture angle is 90 degrees will be described here as well by way of example.

First, as shown in FIG. 15(A), the puncture mechanism 4 has the center part 4D set at the initial position, and the entire outer needle 50 accommodated in the medical fluid administration device 1 and the projection amount of the push-in part 4A from the medical fluid administration device 1 at a maximum.

In this case, the center part 4D has the left and right stopper levers 108A and 108B closed, and the outer needle slide portion 100 fixed to the slide fixing/releasing portion 101, as shown in FIG. 15(B).

Figures 19A, 19B, 19C:
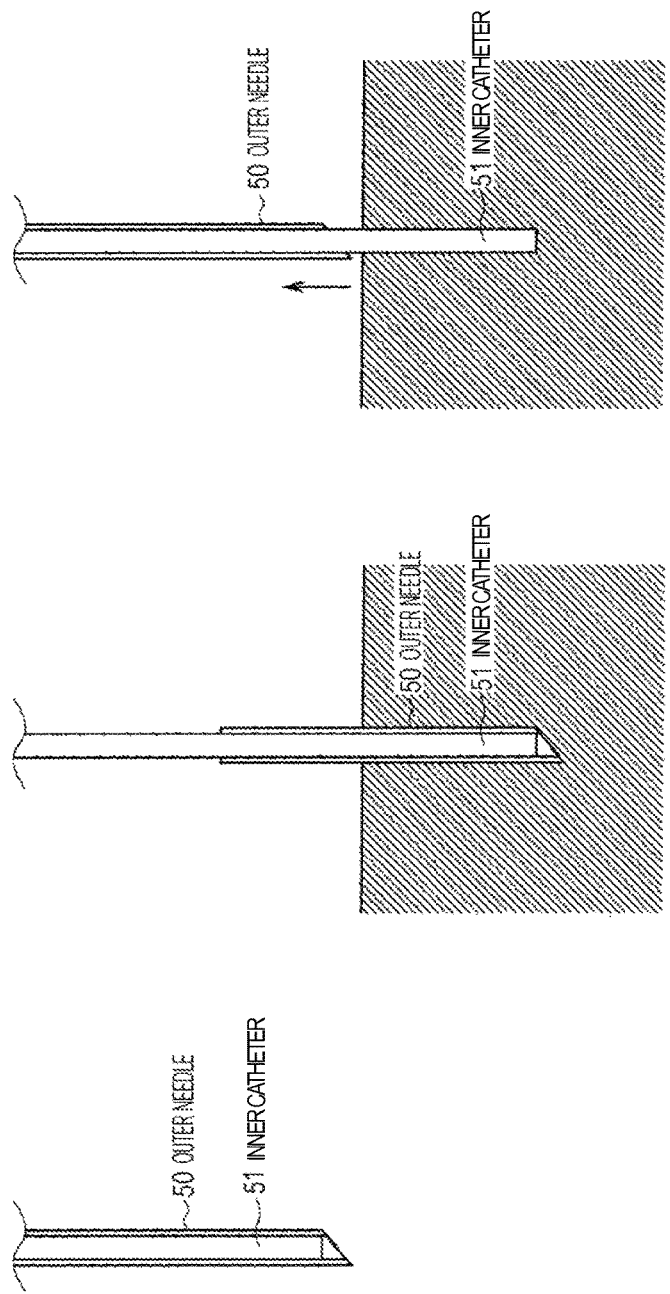
FIGS. 19(A) to 19(C) are schematic diagrams showing a configuration of a puncture needle (outer needle+inner catheter).

Furthermore, as shown in FIG. 19(A), the inner catheter 51 is held on the inner side of the outer needle 50 so that the distal end maintains substantially the same position as the distal end of the outer needle 50 and the position not projecting out from the distal end of the outer needle 50.

After the user attaches the medical fluid administration device 1 to a predetermined position of the body, the push-in part 4A is pushed into the medical fluid administration device 1.

The force of pushing the push-in part 4A downward is transmitted to the center part 4D as a force of sliding the center part 4D toward the lower side through the coupling part 4E, so that the center part 4D is slid toward the lower side through the inner side of the base 4C.

When the center part 4D is slid toward the lower side in such manner, the belt portion 89 fixed to the slide fixing/releasing portion 101 of the center part 4D slides the slide portion 87 in the inner catheter guide part 4F toward the front side accompanying therewith to pull the inner catheter 51.

Thus, the inner catheter 51 reliably moves with the outer needle 50 with the distal end thereof maintaining substantially the same position as the distal end of the outer needle 50 and the position not projecting out from the distal end of the outer needle 50.

When the center part 4D is further slid toward the lower side, the interval of the inner catheter guide part 4F and the center part 4D is widened, and the inner catheter 51 is exposed to the outside of the inner catheter guide part 4F in such range.

The portion positioned between the inner catheter guide part 4F and the center part 4D in the entire inner catheter 51 may be bent with the sliding of the center part 4D if there is nothing to be guided with.

Thus, in the puncture mechanism 4 of the present embodiment, such portion is protected by being inserted into the inner catheter bend preventing portion 92.

In other words, the inner catheter bend preventing portion 92 guides the portion positioned between the inner catheter guide part 4F and the center part 4D of the entire inner catheter 51, thus preventing such portion from bending.

Furthermore, the coil spring 111 having the other end fixed to the outer needle slide portion 100 of the center part 4D is extended, as shown in FIG. 17(B), while the center part 4D is slid toward the lower side in the above manner.

The outer needle 50 of the center part 4D is slid toward the lower side while interiorly holding the inner catheter 51, and passed through the communication hole 70 of the bottom portion 59 of the base 4C and projected out from the puncture needle hole 2C to be punctured into the body of the user with the inner catheter 51.

Figure 17C:
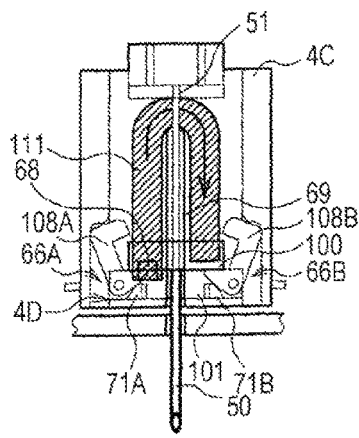

Furthermore, when the push-in part 4A is pushed in and the entire shaft 74 of the push-in part 4A is accommodated in the medical fluid administration device 1, as shown in FIG. 16(A) and FIG. 17(C), the push-in part 4A only has the button 75 projecting out from the medical fluid administration device 1, and hence the projection amount is a minimum.

When the push-in part 4A is pushed in to the end, the center part 4D reaches the lower end of the base 4C. In this case, the outer needle 50 and the inner catheter 51, which are the puncture needle, are punctured the deepest into the body of the user, as shown in FIG. 19(B). In the medical fluid administration device 1, the length of the portion punctured into the body of the user is designed to be 7 mm, for example.

Moreover, in this case, the recessed portions 66A and 66B arranged at the lower ends of the left side wall portion 58A and the right side wall portion 58B are positioned on the outer side of the stopper levers 108A and 108B of the center part 4D. Thus, the stopper levers 108A and 108B are not pushed toward the inner side, and are in the openable state.

The two protrusions 71A and 71B arranged at the bottom portion 59 of the base 4C are brought into contact with the distal end portions of the respective lower side nail portions 109A and 109B of the stopper levers 108A and 108B thus pushing up the distal end portions of the lower side nail portions 109A and 109B, so that the stopper levers 108A and 108B rotate and open toward the outer side.

As a result, as shown in FIG. 16(B), the fixing of the slide fixing/releasing portion 101 of the center part 4D and the outer needle slide portion 100 is released.

That is, the two protrusions 71A and 71B arranged on the bottom portion 59 of the base 4C function as releasing portions that release the fixing of the slide fixing/releasing portion 101 and the outer needle slide portion 100 by the stopper levers 108A and 108B by making contact with the stopper levers 108A and 108B.

Figure 17D:
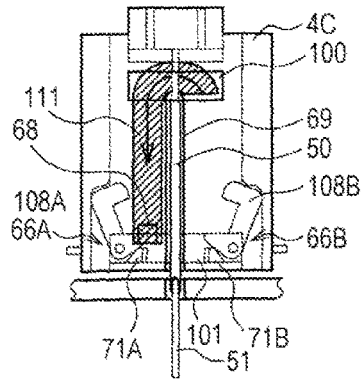
Figure 18A:
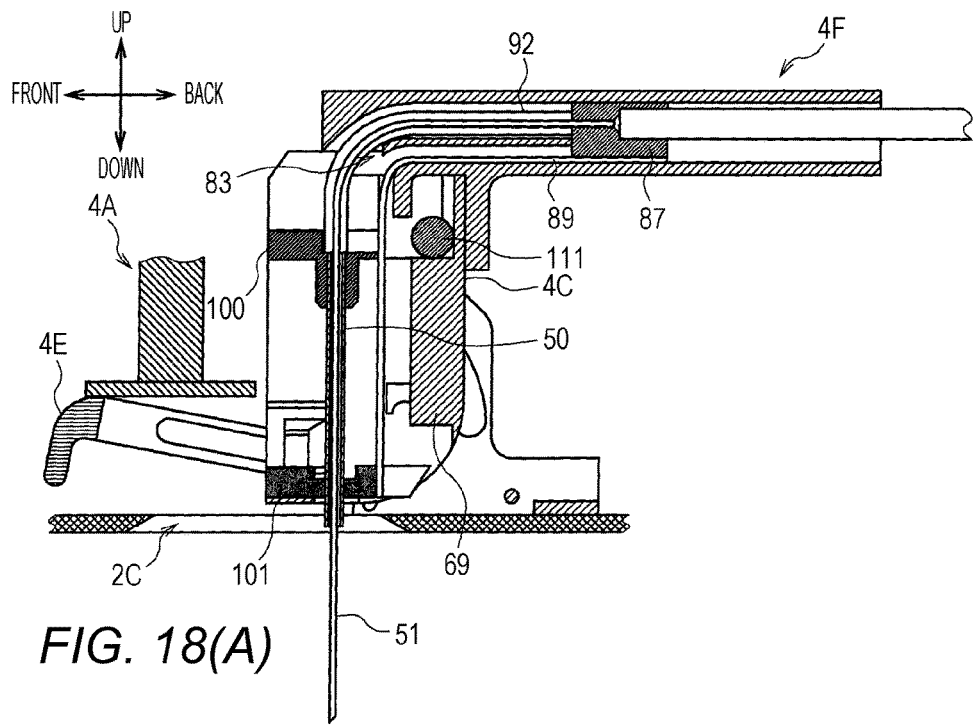
FIGS. 18(A) and 18(B) are schematic diagrams involved in the description of the operation of the puncture mechanism.
Figure 18B:
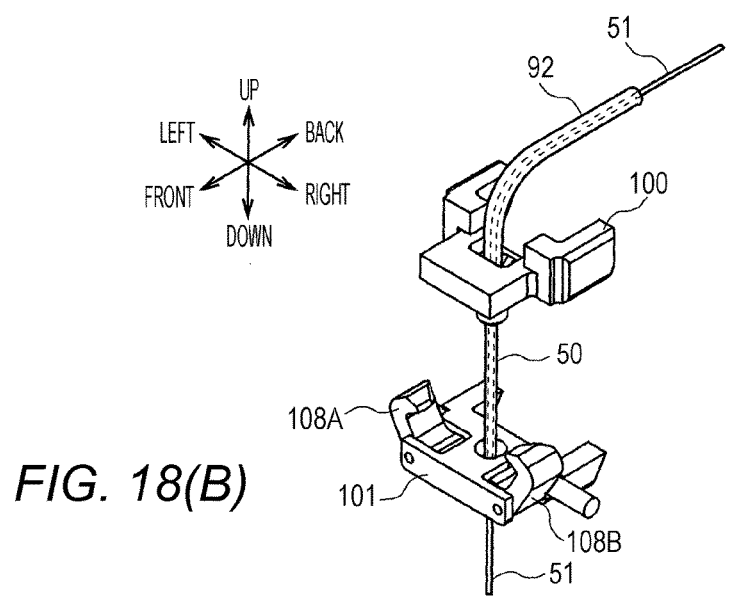

After the fixing is released in such manner, the outer needle slide portion 100 is slid toward the upper side to return to the original position, as shown in FIG. 17(D) and FIGS. 18(A) and 18(B) by the restoring force of the coil spring 111.

The entire outer needle 50 is thus pulled out from the body of the user and accommodated in the medical fluid administration device 1. In this case, the inner catheter 51 is indwelled in the body of the user as is, as shown in FIG. 19(C), by being held at the position by the inner catheter pulling part 90 fixed to the slide fixing/releasing portion 101.

When the outer needle slide portion 100 is slid to the upper side as well, at least the portion positioned between the inner catheter guide part 4F and the outer needle slide portion 100 of the entire inner catheter 51 is covered and guided by the inner catheter bend preventing portion 92.

Thus, the relevant portion is prevented from being bent with the sliding of the outer needle slide portion 100.

As the inner catheter 51 is prevented from being bent between the inner catheter guide part 4F and the outer needle slide portion 100, the inner catheter 51 can also be prevented from falling out from the body of the user, or the portion indwelled in the body of the user can be prevented from becoming short. That is, the inner catheter 51 can be more reliably punctured into the body of the user.

After the inner catheter 51 is punctured into the body of the user with the outer needle 50 in accordance with the push-in operation of the push-in part 4A, and the push-in part 4A is pushed in until the center part 4D reaches the lower end of the base 4C, that is, the push-in part 4A is pushed in to the end, the puncture mechanism 4 pulls out only the outer needle 50 with the inner catheter 51 indwelled in the body.

As described above, in the medical fluid administration device 1, when the push-in part 4A is pushed in by the user, the center part 4D including the outer needle 50 is slid toward the lower side and the inner catheter pulling part 90 fixed to the center part 4D pulls the inner catheter 51, so that the outer needle 50 and the inner catheter 51 inserted into the outer needle 50 are projected out from the medical fluid administration device 1 and punctured into the body of the user.

In the medical fluid administration device 1, when the push-in part 4A is pushed in to the end, the stopper levers 108A and 108B of the center part 4D are opened, and only the outer needle slide portion 100 of the center part 4D is returned to the original position by the restoring force of the coil spring 111, so that only the outer needle 50 is pulled back into the medical fluid administration device 1 with the inner catheter 51 indwelled in the body of the user.

Thereafter, the medical fluid administration device 1 administers the medical fluid stored in the medical fluid storage unit 6 into the body of the user through the inner catheter 51 by means of the feeding unit 8.

Thus, the medical fluid administration device 1 can easily reduce the diameter of the indwelling needle compared to the conventional puncture needle in which the outer needle 50 is the indwelling needle by having the inner catheter 51 of the puncture needle, which has a double structure, as the indwelling needle.

In other words, the medical fluid administration device 1 can have the inner catheter 51 serving as the indwelling needle, which is the portion to be indwelled in the body of the user, formed narrow, so that the burden on the user can be alleviated.

The inner catheter 51 made of resin material can be manufactured in a thin thickness tube, and can have a large inner diameter compared to the metal needle having the same outer diameter.

Furthermore, the medical fluid administration device 1 can carry out the operations of the puncturing the puncture needle (outer needle 50 and inner catheter 51) to the pulling back of the outer needle 50 all at once with merely the push-in operation on the push-in part 4A.

Thus, the puncture mechanism 4 of the medical fluid administration device 1 is operated with only the push-in operation of the user, whereby the drive unit such as the motor, and the like is not necessary, the configuration thereof can be simplified, and the miniaturization can be easily achieved.

Moreover, the medical fluid administration device 1 is configured to pull the inner catheter 51 by the inner catheter pulling part 90 fixed to the outer needle slide portion 100 with the sliding of the outer needle slide portion 100 by the pushing in of the push-in part 4A at the time of puncture, so that the inner catheter 51 and the outer needle 50 can both be reliably moved.

Therefore, for example, a situation where only the outer needle 50 is moved and only the outer needle 50 is punctured into the body of the user can be prevented, and the inner catheter 51 can be reliably punctured into the body of the user with the outer needle 50.

Furthermore, the medical fluid administration device 1 becomes a compact size with fewer protruding portions as a whole when the push-in part 4A is pushed in to the end, whereby the convenience in carrying around can also be enhanced.

7. Configuration of Puncture Angle Adjustment Mechanism

A configuration of the puncture angle adjustment mechanism 5 will now be described in detail. As described above, the puncture angle adjustment mechanism 5 is a mechanism that tilts (moves to change the tilt) the base 4C of the puncture mechanism 4 with respect to the fixed part 4B so that the puncture angle of the outer needle 50 of the puncture needle projecting out from the base 4C can be adjusted within a range of 90 degrees to 30 degrees.

Figure 20:
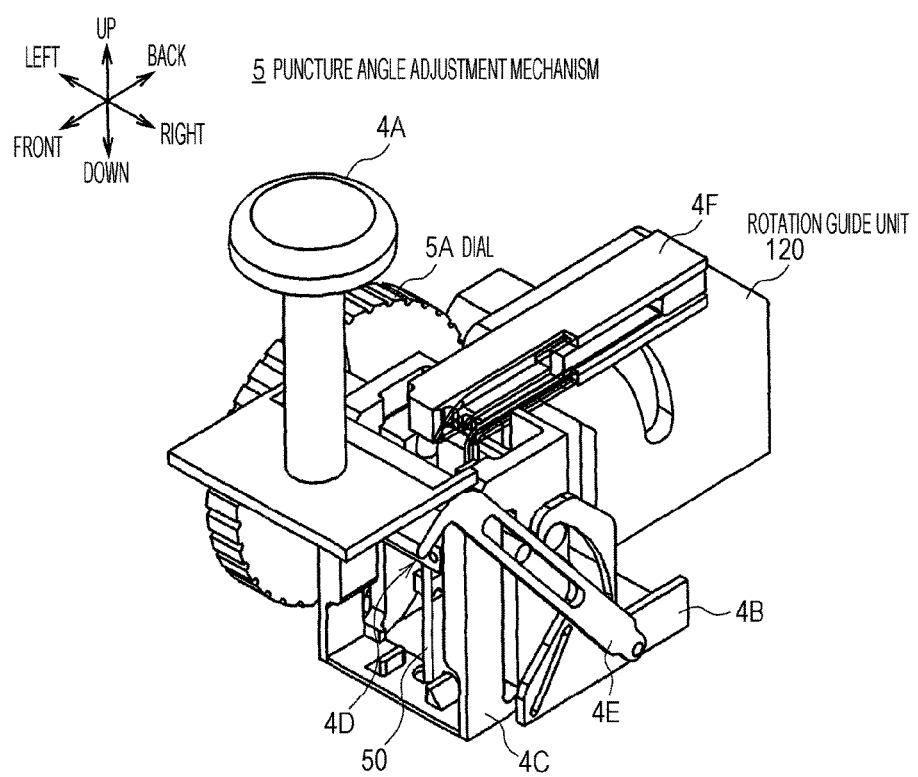
FIG. 20 is a schematic diagram showing a configuration of a puncture angle adjustment mechanism.

As shown in FIGS. 20 and 21, the puncture angle adjustment mechanism 5 mainly includes the puncture mechanism 4 (push-in part 4A, fixed part 4B, base 4C, center part 4D, coupling part 4E, inner catheter guide part 4F), the dial 5A, and a rotation guide unit 120 that acts as a guide when the inner catheter guide part 4F tilts with the base 4C. The configuration of the puncture mechanism 4 has been described above, and thus the description thereof will be omitted here.

As shown in FIG. 21, the dial 5A is substantially disc shaped, where circular column shaped protrusions 121A and 121B, which become rotation shafts of the dial 5A, are arranged in a projecting manner at the center of one side surface of the circle and the center of the other side surface on the opposite side. A hole (also referred to as rotation hole) 122 extending in a radial direction from the vicinity of the center toward the vicinity of the circumferential side surface is formed in the side surface of the dial 5A.

Furthermore, a groove 123 parallel to the thickness direction of the dial 5A is formed at every predetermined interval on the circumferential side surface of the dial 5A.

A pair of plate-shaped dial supporting boards 124A and 124B are arranged in a projecting manner with a predetermined spacing to the left and the right at the vicinity of the left side of the fixed part 4B in the interior on the front end side of the bottom surface 2A of the lower housing unit 2. Shaft holes 125A and 125B are formed at the upper end portions of the dial supporting boards 124A and 124B.

The dial 5A is sandwiched between the dial supporting boards 124A and 124B, and is supported in a freely rotating manner with respect to the dial supporting boards 124A and 124B by fitting the protrusions 121A and 121B into the shaft holes 125A and 125B.

The dial 5A in this case has the third rotation protrusion 64, which is arranged on the left side wall portion 58A of the base 4C supported in a freely rotating manner by the fixed part 4B, fitted into the rotation hole 122.

Thus, as the third rotation protrusion 64 of the base 4C is fitted into the rotation hole 122 of the dial 5A, the base 4C is rotated accompanying the rotation of the dial 5A when the dial 5A is rotated.

A rotation holding portion 126 including a columnar elastic member is arranged in a projecting manner at the back side of the dial supporting boards 124A and 124B in the interior of the front end side of the bottom surface 2A of the lower housing unit 2. The rotation holding portion 126 includes a nail portion 126A that projects out toward the front side (dial 5A side) at the upper end portion of the rotation holding portion 126, where the distal end of the nail portion 126A is to be fitted into the groove 123 formed on the circumferential side surface of the dial 5A supported by the dial supporting boards 124A and 124B.

Thus, the rotation position of the dial 5A can be held by fitting the nail portion 126A of the rotation holding portion 126 into the groove 123 of the dial 5A.

Furthermore, when the dial 5A is rotated, a series of operations in which the nail portion 126A including the elastic member is removed from the groove 123 of the dial 5A, and then fitted into the next groove 123 is repeated.

Therefore, the user rotating the dial 5A can feel the click feeling of "click" every time the user rotates the dial 5A by a predetermined angle.

If the groove 123 is formed every five degrees, for example, on the circumferential side surface of the dial 5A, the rotation holding portion 126 can hold the dial 5A in units of five degrees, so that the user can feel the click feeling every five degrees.

The rotation guide unit 120 has a plate shape parallel in the front and back direction, and is arranged in a projecting manner at a position closer to the left on the back side of the fixed part 4B in the interior of the front end side of the bottom surface 2A of the lower housing unit 2.

The rotation guide unit 120 includes a hole (also referred to as rotation hole) 127 extending in a curved shape from the upper end to the middle at the side surface thereof. The rotation hole 127 has a curved shape bulged toward the back side.

The rotation guide unit 120 has the rotation protrusion 91 arranged in a projecting manner on the left side surface of the inner catheter guide part 4F fitted into the rotation hole 127, where the rotation of the inner catheter guide part 4F is guided by sliding the rotation protrusion 91 in the rotation hole 127.

The puncture angle adjustment mechanism 5 configured as above adjusts the puncture angle by tilting the base 4C supported in a freely tilting manner by the fixed part 4B with the rotation of the dial 5A.

Specifically, assuming the puncture angle of when the angle of the up and down direction of the base 4C (i.e., sliding direction of the center part 4D) and the bottom surface 2A of the lower housing unit 2 is 90 degrees is 90 degrees and the puncture angle of when the angle of the up and down direction of the base 4C (sliding direction of the center part 4D) and the bottom surface 2A of the lower housing unit 2 is 30 degrees is 30 degrees, the puncture angle can be freely adjusted within the range of 90 degrees to 30 degrees by tilting the base 4C within such range.

8. Operation of Puncture Angle Adjustment Mechanism

An operation of the puncture angle adjustment mechanism 5 when actually adjusting the puncture angle will be described in detail with the inclusion of the operation of the puncture mechanism 4.

Figure 22A:
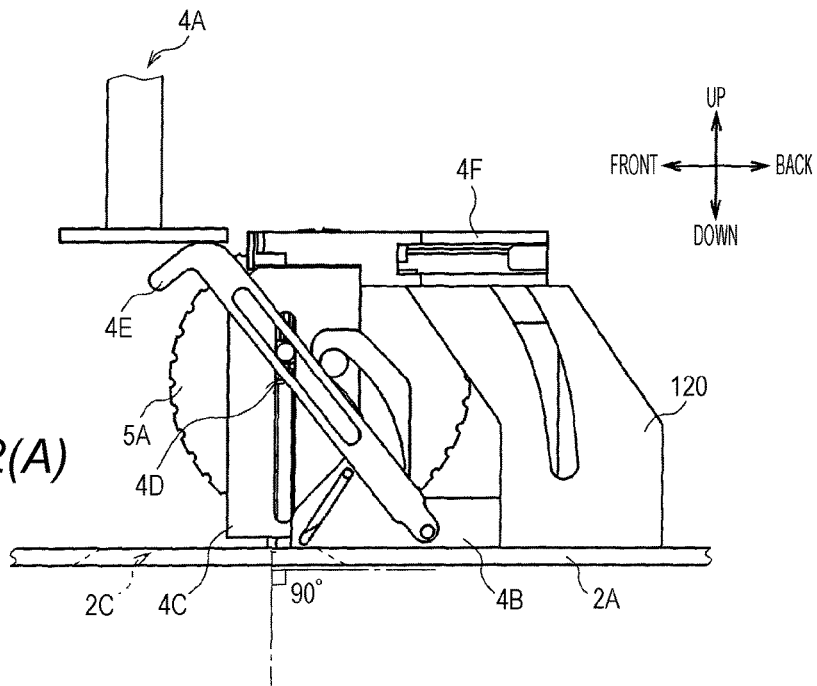
FIGS. 22(A) and 22(B) are schematic diagrams involved in the description of the operation of the puncture angle adjustment mechanism.

As shown in FIG. 22(A), the puncture angle adjustment mechanism 5 has the puncture angle set to 90 degrees as an initial angle, for example.

The user attaches the medical fluid administration device 1 to a predetermined position on the body as is, and then pushes the push-in part 4A into the medical fluid administration device 1.

Figure 22B:
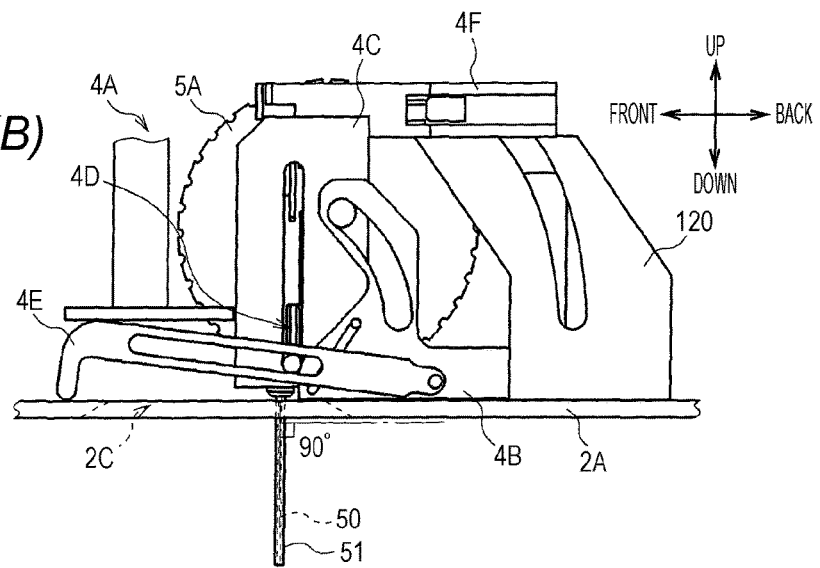

When the puncture mechanism 4 is operated as shown in FIGS. 22(A) and 22(B), the puncture needle (outer needle 50 and inner catheter 51) are punctured into the body of the user at the puncture angle of 90 degrees. After the push-in part 4A is pushed in to the end, the outer needle 50 is pulled back into the medical fluid administration device 1 with the inner catheter 51 indwelled in the body of the user by the puncture mechanism 4. The details of the operation of the puncture mechanism 4 have been described above, and thus the description thereof will be omitted.

The user rotation operates the dial 5A until the puncture angle becomes 45 degrees, for example.

Figure 23A:
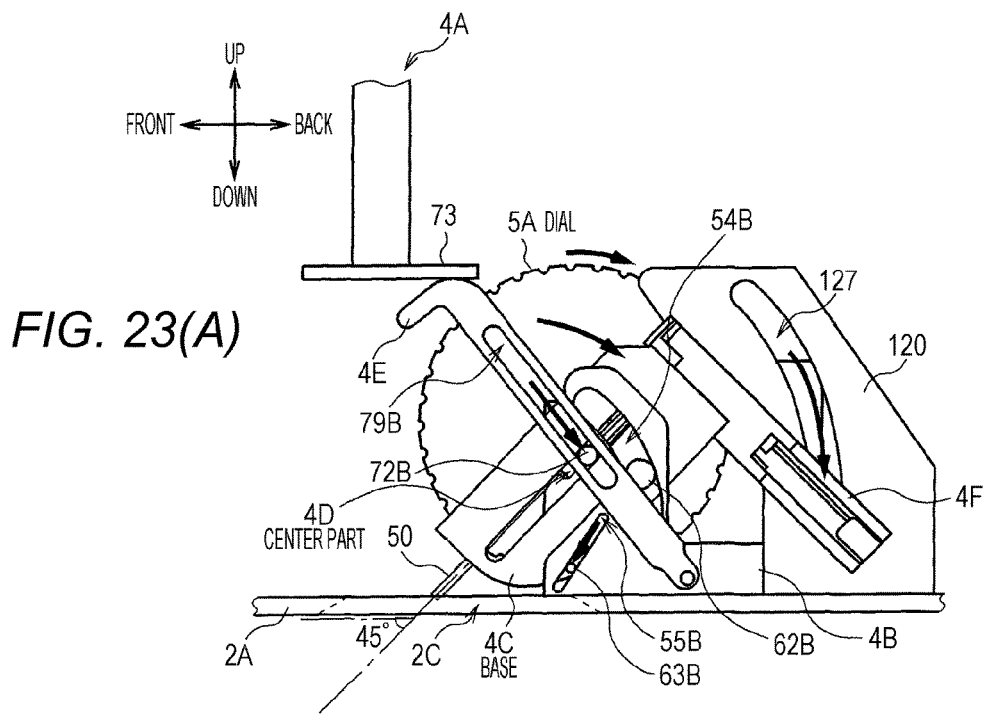
FIGS. 23(A) and 23(B) are schematic diagrams involved in the description of the operation of the puncture angle adjustment mechanism.

As shown in FIG. 23(A), the base 4C is tilted with respect to the fixed part 4B with the rotation of the dial 5A.

Specifically, the base 4C is tilted to fall toward the back side with the second rotation protrusions 63A and 63B fitted into the second rotation holes 55A and 55B of the fixed part 4B as the rotation shafts.

In this case, the base 4C is tilted by sliding the second rotation protrusions 63A and 63B from the upper end toward the lower end of the second rotation holes 55A and 55B of the fixed part 4B, that is by rotating the rotation shaft while moving toward the forward diagonally lower side along the second rotation holes 55A and 55B.

In this case, the base 4C is tilted while sliding the first rotation protrusions 62A and 62B from the upper end toward the lower end of the first rotation holes 54A and 54B of the fixed part 4B, that is, so that the tilting direction is guided by the first rotation holes 54A and 54B.

Thus, the base 4C is tilted to fall toward the back side while moving the rotation shaft toward the forward diagonally lower side, that is, so as to approach the bottom surface 2A of the lower housing unit 2.

The third rotation protrusion 64 of the base 4C is slid from the circumferential side surface side of the rotation hole 122 of the dial 5A toward the center with the rotation of the dial 5A. The rotation of the dial 5A, rotated with the rotation shaft fixed, thus can be smoothly transmitted to the tilting base 4C by moving and rotating the rotation shaft.

The base 4C has the back part of the lower end formed to a curved shape as if the corner is rounded, so that when tilted to fall toward the back side, the back part of the lower end can be smoothly tilted without getting caught at the bottom surface 2A of the lower housing unit 2.

The inner catheter guide part 4F is also tilted accompanying the tilting of the base 4C. In other words, the inner catheter guide part 4F is tilted to fall toward the back side with the tilting of the base 4C so as to fall toward the back side.

Actually, the inner catheter guide part 4F is tilted with the tilting of the base 4C since the slide portion 87 is fixed to the center part 4D fitted into the inner side of the base 4C through the belt portion 89 of the inner catheter pulling part 90.

In this case, the inner catheter guide part 4F is tilted while sliding the rotation protrusion 91 from the upper end toward the lower end of the rotation hole 127 of the rotation guide unit 120, that is, so that the tilting direction is guided by the rotation hole 127.

Thus, the inner catheter guide part 4F is tilted while constantly maintaining the position relationship with the base 4C.

The base 4C and the inner catheter guide part 4F are thus tilted in such manner, and the base 4C and the inner catheter guide part 4F are tilted until the angle of the sliding direction of the center part 4D and the bottom surface 2A of the lower housing unit 2 becomes 45 degrees.

As a result, the puncture angle, which is the angle of the bottom surface 2A of the lower housing unit 2 and the sliding direction of the center part 4D, that is, the attachment surface and the puncture needle (outer needle 50 and inner catheter 51) becomes 45 degrees.

When the user terminates the rotation operation of the dial 5A after rotating the dial 5A until the puncture angle becomes 45 degrees, the dial 5A is held at the relevant rotation position by the rotation holding portion 126 so that the tilt of the base 4C is held, whereby the puncture angle is held at 45 degrees.

While the base 4C is being tilted, the push-in protrusions 72A and 72B of the center part 4D fitted into the inner side of the base 4C are moved toward the backward diagonally lower side with the tilting of the base 4C.

The coupling part 4E, to which the push-in protrusions 72A and 72B of the center part 4D are fitted, includes push-in holes 79A and 79B so as to line along the movement path of the push-in protrusions 72A and 72B.

Thus, even if the push-in protrusions 72A and 72B of the center part 4D are moved with the tilting of the base 4C, the push-in protrusions 72A and 72B of the center part 4D merely move in the push-in holes 79A and 79B of the coupling part 4E, and the coupling part 4E itself does not rotate.

Thus, in the puncture angle adjustment mechanism 5, even if the puncture angle is changed, the position of the coupling part 4E does not change, whereby the coupling part 4E constantly makes contact with the seating part 73 of the push-in part 4A regardless of the puncture angle.

After the user attaches the medical fluid administration device 1, in which the puncture angle is adjusted to 45 degrees, to the predetermined position on the body, the user pushes the push-in part 4A into the medical fluid administration device 1.

Figure 23B:
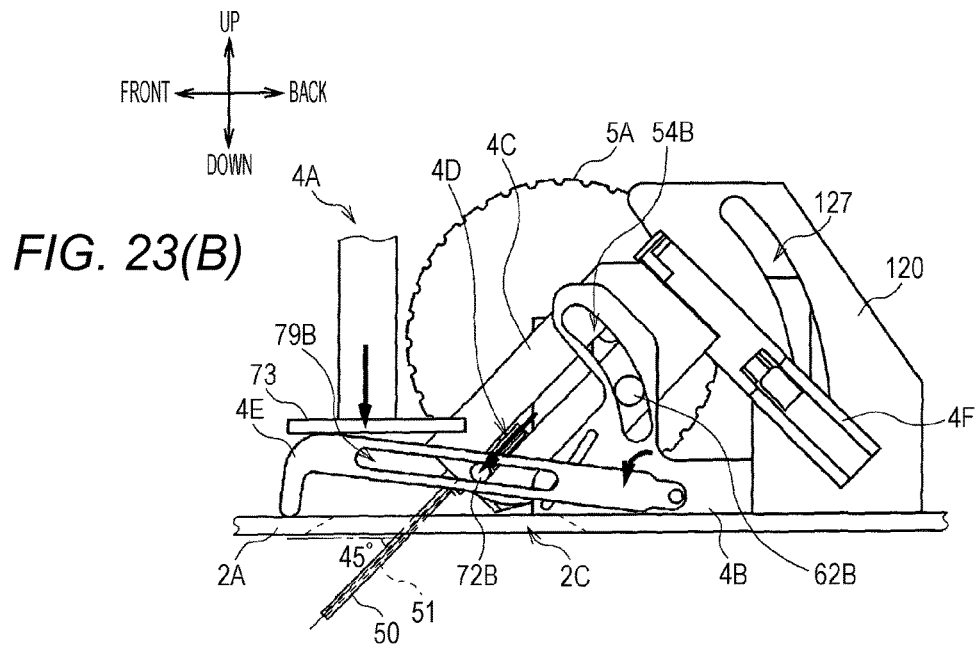

As shown in FIG. 23(B), the force of pushing the push-in part 4A downward is transmitted to the center part 4D as a force of sliding the center part 4D toward the forward diagonally lower side (sliding at an angle of 45 degrees with respect to the bottom surface 2A of the lower housing unit 2) through the coupling part 4E, so that the center part 4D is slid toward the forward diagonally lower side.

The outer needle 50 of the center part 4D is slid at an angle of 45 degrees with respect to the bottom surface 2A of the lower housing unit 2 while holding the inner catheter 51 on the inner side, and projected out from the puncture needle hole 2C through the communication hole 70 of the bottom portion 59 of the base 4C so as to be punctured into the body of the user at the puncture angle of 45 degrees along with the inner catheter 51.

In the puncture angle adjustment mechanism 5, the projecting position from the bottom surface 2A of the puncture needle becomes closer to the front side of the bottom surface 2A the smaller the puncture angle, and thus the puncture needle hole 2C is formed long in the front and back direction in accordance therewith.

When the push-in part 4A is pushed in to the end, the center part 4D reaches the lower end of the base 4C in this case. The outer needle 50 and the inner catheter 51, which are the puncture needle, are punctured the deepest into the body of the user.

The center part 4D has the back end portion tilted as if the corner is cut off, as shown in FIG. 16(A), and thus can be reliably slid to the lower end of the base 4C even in a state the base 4C is fallen toward the back side.

After the push-in part 4A is pushed in to the end in such manner, the outer needle 50 is pulled back into the medical fluid administration device 1 with the inner catheter 51 indwelled in the body of the user by the puncture mechanism 4.

The dial 5A is rotated until the puncture angle becomes 45 degrees in this case, but the puncture angle may be reduced to 30 degrees by further rotating the dial 5A in the same direction in the puncture angle adjustment mechanism 5.

Thus, the medical fluid administration device 1 can freely adjust the puncture angle in the range of 90 degrees to 30 degrees with the puncture angle adjustment mechanism 5, and can carry out the operations of the puncturing the puncture needle (outer needle 50 and inner catheter 51) to the pulling back of the outer needle 50 always with the same operation without changing the push-in direction of the push-in part 4A even if the puncture angle is changed.

As described up to this point, the medical fluid administration device 1 tilts the base 4C with respect to the fixed part 4B when the dial 5A is rotated by the user so that the puncture angle can be adjusted.

Thus, the medical fluid administration device 1 can adjust the puncture angle according to the physique, the subcutaneous thickness, and the like of the user, so that the effect of the medical fluid to be administered can be fully exerted, and hence the usability can be enhanced.

When adjusting the puncture angle in such manner, the position of the center part 4D that can slide on the inner side of the base 4C is changed with the tilting of the base 4C, but the coupling part 4E that couples the push-in part 4A and the center part 4D continues to always couple the push-in part 4A and the center part 4D regardless of the rotation of the base 4C.

In other words, the coupling part 4E always transmits the force at which the push-in part 4A is pushed to the center part 4D as the force of sliding the center part 4D regardless of the rotation of the base 4C.

Thus, the medical fluid administration device 1 can carry out the operations of the puncturing the puncture needle (outer needle 50 and inner catheter 51) to the pulling back of the outer needle 50 always with the same operation of pushing the push-in part 4A downward regardless of the puncture angle.

In other words, the medical fluid administration device 1 can change the puncture angle without changing the push-in direction of the push-in part 4A.

Furthermore, in the medical fluid administration device 1, the puncture angle can be decreased by rotating the dial 5A in one direction, and the puncture angle can be increased by rotating the dial 5A in the other direction, so that the adjustment of the puncture angle can be carried out over a number of times, and even a microscopic adjustment can be easily performed.

Moreover, in the medical fluid administration device 1, the base 4C itself is tilted to adjust the puncture angle, so that the puncture angle can be adjusted without bending the outer needle 50 itself, for example.

Furthermore, the puncture angle adjustment mechanism 5 of the medical fluid administration device 1 is operated with only the dial operation of the user, whereby the drive unit such as the motor, and the like is not necessary, the configuration thereof can be simplified and the miniaturization can be easily achieved.

9. Electrical Configuration of Medical Fluid Administration Device

Figure 24:
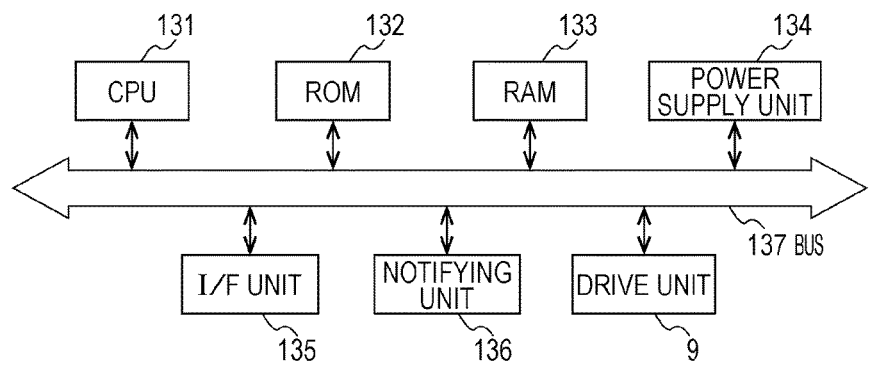
FIG. 24 is a schematic diagram showing an electrical configuration of the medical fluid administration device.

As shown in FIG. 24, the medical fluid administration device 1 has a CPU (Central Processing Unit) 131, a ROM (Read Only Memory) 132, a RAM (Random Access Memory) 133, a power supply unit 134, an interface unit (I/F unit) 135, a notifying unit 136 and the drive unit 9 connected by way of a bus 137.

The CPU 131, the ROM 132, the RAM 133, the power supply unit 134, and the notifying unit 136 are arranged on the substrate unit 10. A battery may be used as the power supply unit 134. A speaker may be used as the notifying unit 136.

The interface unit 135 may be a button (not shown) arranged on the upper housing unit 3 or the lower housing unit 2 to accept input commands of the user.

The CPU 131 reads out a basic program stored in the ROM 132 to the RAM 133 and executes the program to comprehensively control entirety, and reads out various types of administration programs stored in the ROM 132 to the RAM 133 and executes the administration programs to execute various types of processes.

When administering the medical fluid to the user, the CPU 131 reads out a medical fluid administration program to the RAM 133 and executes the medical fluid administration process, so that the medical fluid is externally filled into the medical fluid storage unit 6, and sets parameters such as the administration amount, the administration speed, and the like input through the interface unit 135 after the attachment unit 2B is attached to the skin of the user and the puncture needle is punctured into the skin of the user by the puncture mechanism 4.

The CPU 131 then controls the drive unit 9 based on the set parameters to start the administration of the medical fluid.

10. Alternative Embodiments

10-1. First Alternative Embodiment

In the embodiment described above, a case of applying the present invention to the medical fluid administration device 1 for administering medical fluid to the body of the user has been described. This is not the sole case, and the present invention may be applied to devices other than the medical fluid administration device 1 as long as the device is a puncture device that punctures the puncture needle having a double structure including the outer needle and the inner catheter.

For example, application can be made to a sensor device that inserts various types of sensors into the body of the user to acquire biological information.

Figure 25:
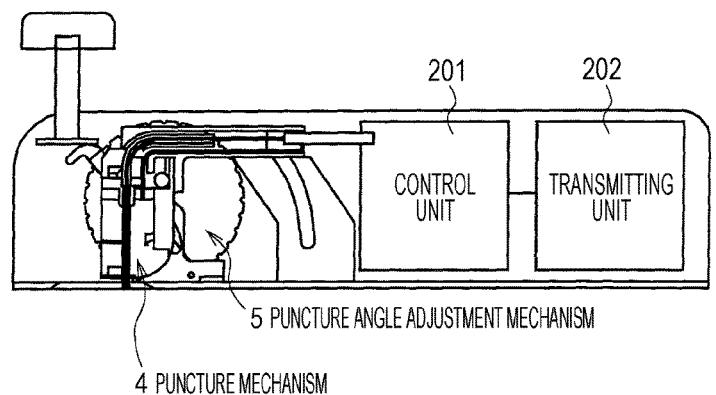
FIG. 25 is a schematic diagram showing a configuration of a sensor device according to an alternative embodiment.

FIG. 25 shows a sensor device 200. The sensor device 200 includes the puncture mechanism 4 and the puncture angle adjustment mechanism 5 similar to the medical fluid administration device 1, but does not include the medical fluid storage unit 6, the feeding unit 8, and the drive unit 9, and instead includes a control unit 201 for acquiring the biological information from the sensor and a transmitting unit 202 for wirelessly transmitting the biological information to the outside.

Figure 26:
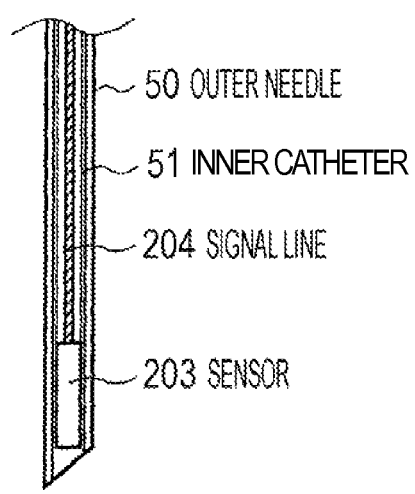
FIG. 26 is a schematic diagram showing a configuration of a puncture needle according to an alternative embodiment.

Furthermore, as shown in FIG. 26, a sensor 203 is attached to the distal end of the inner catheter 51 of the sensor device 200, and furthermore, a signal line 204 that electrically connects the sensor 203 and the control unit 201 is inserted into the inner catheter 51.

In the sensor device 200, the outer needle 50 inserted with the inner catheter 51, in which the sensor 203 is attached at the distal end portion, is punctured into the body of the user by the puncture mechanism 4.

The sensor device 200 pulls back only the outer needle 50 into the sensor device 200 with the sensor 203 indwelled in the body of the user.

Thereafter, the control unit 201 of the sensor device 200 acquires the biological information obtained from the sensor 203, and wirelessly transmits the biological information to the outside through the transmitting unit 202.

10-2. Second Alternative Embodiment

In the embodiment described above, the puncture needle (outer needle 50 and inner catheter 51) is punctured into the body of the user and only the outer needle 50 is pulled back by the puncture mechanism 4 described above, but the puncturing of the puncture needle and the pulling back of the outer needle may be carried out by a puncture mechanism having a configuration different from the puncture mechanism 4 described above.

10-3. Third Alternative Embodiment

In the embodiment described above, when the push-in part 4A is pushed in by the user, the coupling part 4E is rotated by such force, so that the center part 4D connected to the coupling part 4E is slid on the inner side of the base 4C.

This is not the sole case, and for example, an operation unit such as a button, and the like, and a drive unit that automatically rotates the coupling part 4E may be arranged on the medical fluid administration device 1 in place of the push-in part 4A, and the center part 4D may be slid as the drive unit is driven thus rotating the coupling part 4E when the button is pushed by the user.

Figure 27A:
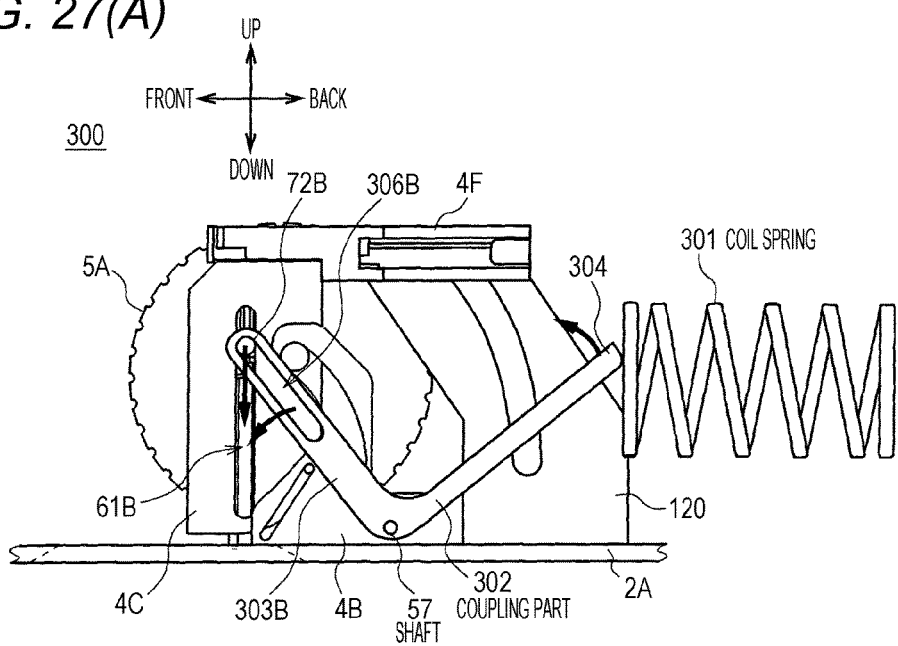
FIGS. 27(A) and 27(B) are schematic diagrams showing a configuration of a puncture angle adjustment mechanism according to the alternative embodiment.

A configuration example of a puncture angle adjustment mechanism 300 in this case is shown in FIG. 27(A). In the puncture angle adjustment mechanism 300, the push-in part 4A is omitted but a coil spring 301 is arranged instead, and a new coupling part 302 is arranged instead of the coupling part 4E, compared to the puncture angle adjustment mechanism 5.

The portions other than the above are similar to the puncture angle adjustment mechanism 5 described above, and thus the description thereof will be omitted.

Figure 27B:
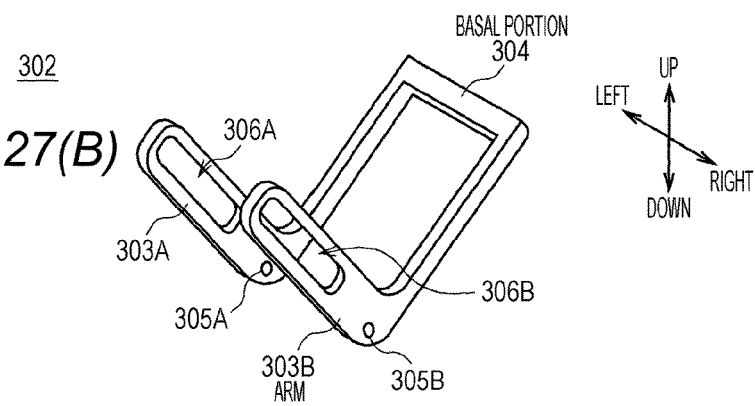

As shown in FIG. 27(B), the coupling part 302 is configured by a pair of left and right L-shaped arms 303A and 303B, and a rectangular plate shaped basal portion 304, which is long in the left and right direction, that connects one end of the arm 303A and one end of the arm 303B.

The arms 303A and 303B include circular rotation holes 305A and 305B at portions (also referred to as corners) corresponding to the L-shaped corner. The arms 303A and 303B include push-in holes 306A and 306B linearly extending from the distal end toward the corner.

The roles of the rotation holes 305A and 305B and the push-in holes 306A and 306B are similar to the coupling part 4E.

In other words, the coupling part 302 is attached to the fixed part 4B in a freely rotating manner by fixing the distal end portion of the shaft 57 fitted into the shaft holes 56A and 56B of the fixed part 4B to the rotation holes 305A and 305B of the arms 303A and 303B.

The coupling part 302 has the distal end portions of the push-in protrusions 72A and 72B of the center part 4D, fitted to the inner side of the base 4C, fitted into the push-in holes 306A and 306B of the arms 303A and 303B.

Furthermore, in this case, the coupling part 302 has the basal portion 304 positioned on the back side of the base 4C, and furthermore, the distal end portion of the coil spring 301 is brought into contact with the back end portion of the basal portion 304.

In other words, the coupling part 302 couples the center part 4D and the coil spring 301.

The coil spring 301 is pushed out forward by the drive unit (not shown) positioned further on the back side thereof.

Actually, when the coil spring 301 is pushed out forward by the drive unit, the basal portion 304 is pushed toward the upper side, so that the coupling part 302 is rotated to lift up the basal portion 304 with the shaft 57 as the rotation shaft.

In this case, the push-in protrusions 72A and 72B of the center part 4D fitted to both the slide holes 61A and 61B of the base 4C and the push-in holes 306A and 306B of the arms 303A and 303B are slid toward the lower side through the slide holes 61A and 61B while sliding toward the corner through the push-in holes 306A and 306B with the rotation of the coupling part 302. As a result, the center part 4D is slid toward the lower side on the inner side of the base 4C.

Thus, the coupling part 302 transmits the force at which the coil spring 301 is pushed in to the center part 4D to slide the center part 4D.

Similar to the coupling part 4E described above, the coupling part 302 has a configuration of constantly continuing to couple the coil spring 301 and the center part 4D regardless of the rotation of the base 4C.

In other words, even in such puncture angle adjustment mechanism 300, the puncture angle can be adjusted without changing the push-in direction of the coil spring 301.

10-4. Fourth Alternative Embodiment

Furthermore, in the embodiment described above, the coil spring 111 is used as an elastic member for pulling back only the outer needle 50 into the medical fluid administration device 1 after the puncture needle including the outer needle 50 made of metal and the inner catheter 51 made of resin is punctured into the body of the user has been described, but this is not the sole case, and an elastic member other than the coil spring 111 may be used as long as the elastic member functions similar to the coil spring 111.

10-5. Fifth Alternative Embodiment

Furthermore, in the embodiment described above, the inner catheter bend preventing portion 92 that covers the inner catheter 51 is arranged between the center part 4D and the front side opening 83 of the inner catheter guide part 4F in the puncture mechanism 4, but this is not the sole case, and the puncture mechanism 4 may have a configuration in which the inner catheter bend preventing portion 92 is omitted.

10-6. Sixth Alternative Embodiment

Furthermore, in the embodiment described above, the inner catheter guide part 4F is tilted while being guided by the rotation guide unit 120 with the tilting of the base 4C.

This is not the sole case, and the inner catheter guide part 4F may be completely fixed with respect to the base 4C, and may be tilted with the tilting of the base 4C even if the rotation guide unit 120 is not arranged.

Accordingly, the rotation guide unit 120 can be omitted, and the configuration can be further simplified.

10-7. Seventh Alternative Embodiment

Further, in the embodiment described above, the user rotation operates the dial 5A serving as the operation unit to adjust the puncture angle, but this is not the sole case, and for example, an operation unit such as a button for specifying the puncture angle and a drive unit for automatically tilting the base 4C may be arranged in the medical fluid administration device 1, where when the puncture angle is specified through the operation unit by the user, the drive unit is driven to tilt the base 4C thus adjusting the puncture angle.

10-8. Eighth Alternative Embodiment

Furthermore, in the embodiment described above, the inner catheter pulling part 90 of the puncture mechanism 4 is configured by the belt-like belt portion 89 and the slide portion 87.

This is not the sole case, and a wire portion including a wire made of metal or made of resin, for example, may be used in place of the belt portion 89, and the inner catheter pulling part 90 may be configured by the wire portion and the slide portion 87.

In this case, the distal end of the wire portion is fixed to the slide fixing/releasing portion 101, and the back end is fixed to the slide portion 87.

This is not the sole case, and a member other than the belt and the wire may be used as long as the member can be freely bent such as with the belt and the wire, and can couple the slide fixing/releasing portion 101 and the slide portion 87.

The present invention can be applied, for example, to medical fields.

What is claimed is:
1. A puncture device comprising:
a housing unit including an attachment surface configured to be attached to a body surface of a user, the housing unit defining a space therein;
a puncture needle including an outer needle and an inner catheter, wherein at least a portion of the inner catheter is located in the outer needle, and wherein the puncture needle is configured to be moved from a first location at which an entirety of the puncture needle is located in the space in the housing unit to a second location at which the puncture needle projects from the attachment surface to be punctured into a body of the user;
a puncture mechanism comprising:
a base configured to act as a guide when sliding the outer needle, a push-in part configured to be pushed with respect to the housing unit,
a center part that is arranged with the outer needle and that slides along the base, and
a coupling part that couples the center part and the push-in part,
wherein the puncture mechanism is configured to cause the puncture needle, in which a distal end portion of the inner catheter is inserted in the outer needle, to project out from the attachment surface by sliding the outer needle along the base, and to pull back only the outer needle of the puncture needle into the housing unit with the inner catheter of the puncture needle indwelled in the body, and
wherein, when the push-in part is pushed in with respect to the housing unit, a force with which the push-in part is pushed in is transmitted to the center part and slides the center part via the coupling part to project the puncture needle from the attachment surface; and
a puncture angle adjustment mechanism configured to adjust a puncture angle of the puncture needle, which is an angle of the puncture needle with respect to the attachment surface, the puncture angle adjustment mechanism comprising:
a fixed part that is fixed to the housing unit and that supports the base in a freely tiltable manner, and
a dial that is accessible from a location outside the housing unit so as to be rotatably operable by a user such that, when the dial is rotated by the user, the rotation of the dial with respect to the fixed part changes a tilt of the base with respect to the fixed part, and the puncture angle is thereby adjusted,
wherein the center part is held on one end side of the base at an initial position before sliding, the initial position being moved as the base is tilted when changing the puncture angle,
wherein the coupling part includes a hole in which a part of the center part is fitted, the coupling part being coupled with the center part by said part of the center part being fitted in the hole, and
wherein the hole of the coupling part is formed along a movement path of the initial position of the center part, and the puncture mechanism is configured such that the coupling of the push-in part and the center part by the coupling part being maintained constantly as the initial position of the center part is moved and a part of the center part is moved along the hole.

2. The puncture device according to claim 1,
wherein the coupling part is attached in a freely rotating manner with respect to the fixed part, and
wherein the coupling part is configured to slide the center part along the base while a part of the center part moves along the hole by rotating with the pushing in of the push-in part.

3. The puncture device according to claim 1,
wherein the housing unit has a top surface, a bottom surface, and a side surface extending from the top surface to the bottom surface; and
wherein the dial is rotatably operable by the user via an opening in the top surface of the housing unit.

4. The puncture device according to claim 1,
wherein, when the rotation of the dial with respect to the fixed part changes a tilt of the base with respect to the fixed part, the tilt of the base is changed with respect to the push in part.

5. A medical fluid administration device comprising:
a housing unit including an attachment surface configured to be attached to a body surface of a user, the housing unit defining a space therein;
a puncture needle including an outer needle and an inner catheter, wherein at least a portion of the inner catheter is located in the outer needle, and wherein the puncture needle is configured to be moved from a first location at which an entirety of the puncture needle is located in the space in the housing unit to a second location at which the puncture needle projects from the attachment surface to be punctured into a body of the user;
a puncture mechanism comprising:
a base configured to act as a guide when sliding the outer needle,
a push-in part configured to be pushed with respect to the housing unit,
a center part that is arranged with the outer needle and that slides along the base, and
a coupling part that couples the center part and the push-in part,
wherein the puncture mechanism is configured to cause the puncture needle, in which a distal end portion of the inner catheter is inserted in the outer needle, to project out from the attachment surface by sliding the outer needle along the base, and to pull back only the outer needle of the puncture needle into the housing unit with the inner catheter of the puncture needle indwelled in the body, and
wherein, when the push-in part is pushed in with respect to the housing unit, a force with which the push-in part is pushed in is transmitted to the center part and slides the center part via the coupling part to project the puncture needle from the attachment surface;
a medical fluid storage unit configured to store a medical fluid;
a feeding unit configured to feed the medical fluid stored in the medical fluid storage unit into the body through the puncture needle; and
a puncture angle adjustment mechanism configured to adjust a puncture angle of the puncture needle, which is an angle of the puncture needle with respect to the attachment surface, the puncture angle adjustment mechanism comprising:
a fixed part that is fixed to the housing unit and that supports the base in a freely tiltable manner, and
a dial that is accessible from a location outside the housing unit so as to be rotatably operable by a user such that, when the dial is rotated by the user, the rotation of the dial with respect to the fixed part changes a tilt of the base with respect to the fixed part, and the puncture angle is thereby adjusted,
wherein the center part is held on one end side of the base at an initial position before sliding, the initial position being moved as the base is tilted when changing the puncture angle,
wherein the coupling part includes a hole in which a part of the center part is fitted, the coupling part being coupled with the center part by said part of the center part being fitted in the hole, and
wherein the hole of the coupling part is formed along a movement path of the initial position of the center part, and the puncture mechanism is configured such that the coupling of the push-in part and the center part by the coupling part being maintained constantly as the initial position of the center part is moved and a part of the center part is moved along the hole.

6. The medical fluid administration device according to claim 5,
wherein the coupling part is attached in a freely rotating manner with respect to the fixed part, and
wherein the coupling part is configured to slide the center part along the base while a part of the center part moves along the hole by rotating with the pushing in of the push-in part.

7. The medical fluid administration device according to claim 5,
wherein the housing unit has a top surface, a bottom surface, and a side surface extending from the top surface to the bottom surface; and
wherein the dial is rotatably operable by the user via an opening in the top surface of the housing unit.

8. The medical fluid administration device according to claim 5,
wherein, when the rotation of the dial with respect to the fixed part changes a tilt of the base with respect to the fixed part, the tilt of the base is changed with respect to the push in part.

9. A puncture device comprising:
a housing unit including a top surface, a bottom surface, a side surface extending from the top surface to the bottom surface, and an attachment surface located at the bottom surface and configured to be attached to a body surface of a user, the housing unit defining a space therein;
a puncture needle including an outer needle and an inner catheter, wherein at least a portion of the inner catheter is located in the outer needle, and wherein the puncture needle is configured to be moved from a first location at which an entirety of the puncture needle is located in the space in the housing unit to a second location at which the puncture needle projects from the attachment surface to be punctured into a body of the user;
a puncture mechanism comprising a base configured to act as a guide when sliding the outer needle, the puncture mechanism being configured to cause the puncture needle, in which a distal end portion of the inner catheter is inserted in the outer needle, to project out from the attachment surface by sliding the outer needle along the base, and to pull back only the outer needle of the puncture needle into the housing unit with the inner catheter of the puncture needle indwelled in the body; and
a puncture angle adjustment mechanism configured to adjust a puncture angle of the puncture needle, which is an angle of the puncture needle with respect to the attachment surface, the puncture angle adjustment mechanism comprising:
a fixed part that is fixed to the housing unit and that supports the base in a freely tiltable manner, and
a dial that is accessible from a location outside the housing unit via an opening in the top surface of the housing unit, so as to be rotatably operable by a user via the opening such that, when the dial is rotated by the user, the rotation of the dial with respect to the fixed part changes a tilt of the base with respect to the fixed part, and the puncture angle is thereby adjusted.

10. A medical fluid administration device comprising:
a housing unit including a top surface, a bottom surface, a side surface extending from the top surface to the bottom surface, and an attachment surface located at the bottom surface and configured to be attached to a body surface of a user, the housing unit defining a space therein;
a puncture needle including an outer needle and an inner catheter, wherein at least a portion of the inner catheter is located in the outer needle, and wherein the puncture needle is configured to be moved from a first location at which an entirety of the puncture needle is located in the space in the housing unit to a second location at which the puncture needle projects from the attachment surface to be punctured into a body of the user;
a puncture mechanism comprising a base configured to act as a guide when sliding the outer needle, the puncture mechanism being configured to cause the puncture needle, in which a distal end portion of the inner catheter is inserted in the outer needle, to project out from the attachment surface by sliding the outer needle along the base, and to pull back only the outer needle of the puncture needle into the housing unit with the inner catheter of the puncture needle indwelled in the body;
a medical fluid storage unit configured to store a medical fluid;
a feeding unit configured to feed the medical fluid stored in the medical fluid storage unit into the body through the puncture needle; and
a puncture angle adjustment mechanism configured to adjust a puncture angle of the puncture needle, which is an angle of the puncture needle with respect to the attachment surface, the puncture angle adjustment mechanism comprising:
a fixed part that is fixed to the housing unit and that supports the base in a freely tiltable manner, and
a dial that is accessible from a location outside the housing unit via an opening in the top surface of the housing unit, so as to be rotatably operable by a user via the opening such that, when the dial is rotated by the user, the rotation of the dial with respect to the fixed part changes a tilt of the base with respect to the fixed part, and the puncture angle is thereby adjusted.

* * * * *